US012636481B2

(12) United States Patent
Nelson et al.

(10) Patent No.: US 12,636,481 B2
(45) Date of Patent: May 26, 2026

(54) MEDICAL CONNECTORS

(71) Applicant: ICU Medical, Inc., San Clemente, CA (US)

(72) Inventors: David Nelson, Laguna Beach, CA (US); Christopher James Hughes, Dana Point, CA (US)

(73) Assignee: ICU Medical, Inc., San Clemente, CA (US)

( * ) Notice: Subject to any disclaimer, the term of this patent is extended or adjusted under 35 U.S.C. 154(b) by 757 days.

(21) Appl. No.: 17/816,839

(22) Filed: Aug. 2, 2022

(65) Prior Publication Data

US 2023/0045573 A1 Feb. 9, 2023

Related U.S. Application Data

(60) Provisional application No. 63/228,982, filed on Aug. 3, 2021.

(51) Int. Cl.
*A61M 39/10* (2006.01)

(52) U.S. Cl.
CPC ..... *A61M 39/10* (2013.01); *A61M 2039/1077* (2013.01); *A61M 2039/1088* (2013.01)

(58) Field of Classification Search
CPC .......... A61M 39/10; A61M 2039/1077; A61M 2039/1088; A61M 39/1055; A61M 39/1011; A61M 2039/1033; A61M 2039/1066
See application file for complete search history.

(56) References Cited

U.S. PATENT DOCUMENTS

| | | | |
|---|---|---|---|
| 2,254,997 | A | 9/1941 | Fisher |
| 2,419,453 | A | 4/1947 | Kocevar |
| 2,456,045 | A | 12/1948 | Brock |

(Continued)

FOREIGN PATENT DOCUMENTS

| | | |
|---|---|---|
| CA | 2747283 | 7/2002 |
| DE | 20 2014 103247 U1 | 8/2014 |

(Continued)

OTHER PUBLICATIONS

Air Embolism and Exsanguination from Separation of Two-Piece Side Port/Hemostasis Valve Cardiac Catheter Introducers, ECRI Institute, Jan. 1995, in 2 pages, http://www.mdsr.ecri.org/summary/detail.aspx?doc_id=8098.

(Continued)

*Primary Examiner* — Jason E Flick
(74) *Attorney, Agent, or Firm* — Knobbe, Martens, Olson & Bear, LLP

(57) ABSTRACT

An adapter for connecting a first connector to a second connector can include a proximal portion configured to linearly engage the first connector with a snap-fit engagement. The adapter can include a distal portion configured to rotationally engage the second connector. Rotation of the adapter relative to the second connector can advance a male luer of the first connector into substantially sealing engagement with a female luer on the second connector. The adapter can be configured to displace a collar on the first connector when coupled to the first connector. The second connector can include a proximal portion that is configured to engage the first connector, such as with a snap-fit engagement.

20 Claims, 17 Drawing Sheets

(56)                References Cited

U.S. PATENT DOCUMENTS

| | | |
|---|---|---|
| 2,457,052 A | 12/1948 | Le Clair |
| 2,485,006 A | 10/1949 | Main, Jr. et al. |
| 2,842,382 A | 7/1958 | Franck |
| 2,931,668 A | 4/1960 | Baley |
| 2,968,497 A | 1/1961 | Treleman |
| 3,127,892 A | 4/1964 | Bellamy, Jr. et al. |
| 3,191,972 A | 6/1965 | Collar |
| 3,304,047 A | 2/1967 | Martin |
| 3,334,860 A | 8/1967 | Bolton, Jr. |
| 3,538,950 A | 11/1970 | Porteners |
| 3,707,972 A | 1/1973 | Villari et al. |
| 3,729,031 A | 4/1973 | Baldwin |
| 3,824,556 A | 7/1974 | Berkovits et al. |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,187,848 A | 2/1980 | Taylor |
| 4,195,632 A | 4/1980 | Parker et al. |
| 4,233,982 A | 11/1980 | Bauer et al. |
| 4,245,635 A | 1/1981 | Kontos |
| 4,286,640 A | 9/1981 | Knox |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,405,312 A | 9/1983 | Gross et al. |
| 4,430,073 A | 2/1984 | Bemis et al. |
| 4,432,759 A | 2/1984 | Gross et al. |
| 4,436,125 A | 3/1984 | Blenkush |
| 4,452,473 A | 6/1984 | Ruschke |
| 4,457,749 A | 7/1984 | Bellotti et al. |
| 4,473,369 A | 9/1984 | Lueders et al. |
| 4,511,359 A | 4/1985 | Vaillancourt |
| 4,538,836 A | 9/1985 | Kruetten |
| 4,541,457 A | 9/1985 | Blenkush |
| 4,576,359 A | 3/1986 | Oetiker |
| 4,596,571 A | 6/1986 | Bellotti et al. |
| 4,607,868 A | 8/1986 | Harvey et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,673,400 A | 6/1987 | Martin |
| 4,700,744 A | 10/1987 | Rutter et al. |
| 4,723,603 A | 2/1988 | Plummer |
| 4,723,948 A | 2/1988 | Clark et al. |
| 4,728,075 A | 3/1988 | Paradis |
| 4,745,950 A | 5/1988 | Mathieu |
| 4,758,023 A | 7/1988 | Vermillion |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,819,692 A | 4/1989 | Olson et al. |
| 4,834,271 A | 5/1989 | Litwin |
| 4,844,512 A | 7/1989 | Gahwiler |
| 4,862,913 A | 9/1989 | Wildfang |
| 4,863,201 A | 9/1989 | Carstens |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,949,745 A | 8/1990 | McKeon |
| 4,950,260 A | 8/1990 | Bonaldo |
| 4,969,879 A | 11/1990 | Lichte |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A * | 9/1991 | Utterberg ................ F16L 33/24 |
| | | 604/905 |
| 5,053,015 A | 10/1991 | Gross |
| 5,065,783 A | 11/1991 | Ogle, II |
| 5,066,286 A | 11/1991 | Ryan |
| 5,070,885 A | 12/1991 | Bonaldo |
| 5,083,819 A | 1/1992 | Bynum |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| 5,176,406 A | 1/1993 | Straghan |
| RE34,223 E | 4/1993 | Bonaldo |
| 5,199,948 A | 4/1993 | McPhee |
| 5,201,717 A | 4/1993 | Wyatt et al. |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,224,939 A | 7/1993 | Holman et al. |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,322,518 A | 6/1994 | Schneider et al. |
| 5,324,270 A | 6/1994 | Kayan et al. |
| 5,330,235 A | 7/1994 | Wagner et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| D358,882 S | 5/1995 | Metz et al. |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,447,177 A | 9/1995 | Ricken et al. |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |

(56)        References Cited

U.S. PATENT DOCUMENTS

| | | | |
|---|---|---|---|
| 5,480,393 A | 1/1996 | Bommarito |
| 5,489,274 A | 2/1996 | Chu et al. |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,531,695 A | 7/1996 | Swisher |
| 5,533,708 A | 7/1996 | Atkinson et al. |
| 5,533,983 A | 7/1996 | Haining |
| 5,533,996 A | 7/1996 | Murphey et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,583 A | 8/1996 | Sanford et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| 5,620,210 A | 4/1997 | Eyster et al. |
| 5,620,427 A | 4/1997 | Werschmidt et al. |
| RE35,539 E | 6/1997 | Bonaldo |
| 5,643,224 A | 7/1997 | Szapiro et al. |
| 5,645,538 A | 7/1997 | Richmond |
| 5,651,776 A * | 7/1997 | Appling ............... A61M 39/10 |
| | | 285/332 |
| D382,958 S | 8/1997 | Wolff |
| 5,658,260 A | 8/1997 | Desecki et al. |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,709,243 A | 1/1998 | Wells et al. |
| 5,735,826 A | 4/1998 | Richmond |
| 5,738,144 A | 4/1998 | Rogers |
| 5,741,084 A | 4/1998 | Del Rio et al. |
| 5,749,861 A | 5/1998 | Guala et al. |
| D395,502 S | 6/1998 | Deily et al. |
| RE35,841 E | 7/1998 | Frank et al. |
| 5,782,816 A | 7/1998 | Werschmidt et al. |
| 5,784,750 A | 7/1998 | Sankovic et al. |
| 5,785,693 A | 7/1998 | Haining |
| 5,788,215 A | 8/1998 | Ryan |
| 5,806,831 A | 9/1998 | Paradis |
| 5,810,398 A | 9/1998 | Matkovich |
| 5,814,024 A | 9/1998 | Thompson et al. |
| 5,820,601 A | 10/1998 | Mayer |
| 5,820,614 A | 10/1998 | Erksine et al. |
| 5,830,189 A | 11/1998 | Chang |
| 5,830,195 A | 11/1998 | Peters et al. |
| 5,839,715 A | 11/1998 | Leinsing |
| 5,848,994 A | 12/1998 | Richmond |
| 5,855,568 A | 1/1999 | Battiato et al. |
| 5,947,954 A | 9/1999 | Bonaldo |
| 5,984,373 A | 11/1999 | Fitoussi et al. |
| 6,029,946 A | 2/2000 | Doyle |
| 6,036,171 A | 3/2000 | Weinheimer et al. |
| 6,039,302 A | 3/2000 | Cote, Sr. et al. |
| 6,041,805 A | 3/2000 | Gydesen et al. |
| 6,050,978 A | 4/2000 | Orr et al. |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,099,519 A | 8/2000 | Olsen et al. |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,168,137 B1 | 1/2001 | Paradis |
| 6,170,522 B1 | 1/2001 | Tanida |
| 6,171,287 B1 | 1/2001 | Lynn et al. |
| 6,183,464 B1 | 2/2001 | Sharp et al. |
| 6,189,859 B1 | 2/2001 | Rohrbough et al. |
| 6,206,860 B1 | 3/2001 | Richmond |
| 6,221,029 B1 | 4/2001 | Mathis et al. |
| 6,224,578 B1 | 5/2001 | Davis et al. |
| 6,224,588 B1 | 5/2001 | Jentzen |
| 6,231,552 B1 | 5/2001 | Jentzen |
| 6,242,393 B1 | 6/2001 | Ishida et al. |
| 6,245,048 B1 | 6/2001 | Fangrow et al. |
| 6,290,206 B1 | 9/2001 | Doyle |
| 6,299,132 B1 | 10/2001 | Weinheimer et al. |
| 6,325,100 B1 | 12/2001 | Bunschoten et al. |
| 6,332,633 B1 | 12/2001 | Fitoussi et al. |
| 6,402,207 B1 | 6/2002 | Segal et al. |
| 6,428,520 B1 | 8/2002 | Lopez |
| 6,431,219 B1 | 8/2002 | Redler et al. |
| 6,439,276 B1 | 8/2002 | Wood et al. |
| D465,843 S | 11/2002 | Guala |
| 6,485,472 B1 | 11/2002 | Richmond |
| 6,499,719 B1 | 12/2002 | Clancy et al. |
| D469,530 S | 1/2003 | Gomez |
| 6,508,792 B2 | 1/2003 | Szames et al. |
| 6,508,807 B1 | 1/2003 | Peters |
| 6,541,802 B2 | 4/2003 | Doyle |
| 6,543,745 B1 | 4/2003 | Enerson |
| 6,581,906 B2 | 6/2003 | Pott et al. |
| 6,585,229 B2 | 7/2003 | Cote et al. |
| 6,595,964 B2 | 7/2003 | Finley et al. |
| 6,595,981 B2 | 7/2003 | Huet |
| 6,605,076 B1 | 8/2003 | Jepson |
| 6,609,696 B2 | 8/2003 | Enerson |
| 6,612,624 B1 | 9/2003 | Segal et al. |
| 6,666,852 B2 | 12/2003 | Niedospial, Jr. |
| 6,673,059 B2 | 1/2004 | Guala |
| 6,681,803 B2 | 1/2004 | Taneya et al. |
| 6,695,817 B1 | 2/2004 | Fangrow |
| 6,745,998 B2 | 6/2004 | Doyle |
| 6,808,161 B1 | 10/2004 | Hishikawa |
| 6,840,501 B2 | 1/2005 | Doyle |
| 6,843,513 B2 | 1/2005 | Guala |
| 6,869,426 B2 | 3/2005 | Ganem |
| 6,875,205 B2 | 4/2005 | Leinsing |
| 6,893,056 B2 | 5/2005 | Guala |
| 6,899,315 B2 | 5/2005 | Mailville et al. |
| 6,911,025 B2 | 6/2005 | Miyahara |
| 6,916,051 B2 | 7/2005 | Fisher |
| 6,955,669 B2 | 10/2005 | Curutcharry |
| 6,964,406 B2 | 11/2005 | Doyle |
| 6,991,608 B2 | 1/2006 | Young et al. |
| 6,997,917 B2 | 2/2006 | Niedospial, Jr. et al. |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,137,654 B2 | 11/2006 | Segal et al. |
| 7,140,592 B2 | 11/2006 | Phillips |
| 7,160,272 B1 | 1/2007 | Eyal et al. |
| D536,958 S | 2/2007 | Ruhlander |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,197 B2 | 12/2007 | Parrino et al. |
| 7,306,198 B2 | 12/2007 | Doyle |
| 7,306,566 B2 | 12/2007 | Raybuck |

(56)　　　　References Cited

U.S. PATENT DOCUMENTS

| | | | |
|---|---|---|---|
| 7,316,679 | B2 | 1/2008 | Bierman |
| 7,347,458 | B2 | 3/2008 | Rome et al. |
| 7,350,764 | B2 | 4/2008 | Raybuck |
| 7,350,834 | B2 | 4/2008 | Ryhman et al. |
| 7,361,164 | B2 | 4/2008 | Simpson et al. |
| D569,973 | S | 5/2008 | Oren et al. |
| 7,396,051 | B2 | 7/2008 | Baldwin et al. |
| 7,448,653 | B2 | 11/2008 | Jensen et al. |
| 7,497,484 | B2 | 3/2009 | Ziman |
| 7,503,596 | B2 | 3/2009 | Rome et al. |
| D590,022 | S | 4/2009 | Misumi |
| D595,420 | S | 6/2009 | Suzuki et al. |
| D595,421 | S | 6/2009 | Suzuki et al. |
| D595,863 | S | 7/2009 | Suzuki et al. |
| 7,559,530 | B2 | 7/2009 | Korogi et al. |
| 7,588,563 | B2 | 9/2009 | Guala |
| 7,600,515 | B2 | 10/2009 | Matlock |
| 7,628,781 | B2 | 12/2009 | Roy et al. |
| 7,645,274 | B2 | 1/2010 | Whitley |
| 7,651,481 | B2 | 1/2010 | Raybuck |
| 7,666,170 | B2 | 2/2010 | Guala |
| D612,939 | S | 3/2010 | Boone, III et al. |
| 7,670,326 | B2 | 3/2010 | Shemesh |
| 7,717,874 | B2 | 5/2010 | Landau et al. |
| 7,722,090 | B2 | 5/2010 | Burton et al. |
| 7,758,566 | B2 | 7/2010 | Simpson et al. |
| 7,762,524 | B2 | 7/2010 | Cawthon et al. |
| 7,763,013 | B2 | 7/2010 | Baldwin et al. |
| 7,766,304 | B2 | 8/2010 | Phillips |
| 7,766,897 | B2 | 8/2010 | Ramsey et al. |
| 7,770,939 | B2 | 8/2010 | Jensen et al. |
| 7,803,139 | B2 | 9/2010 | Fangrow, Jr. |
| 7,803,140 | B2 | 9/2010 | Fangrow, Jr. |
| 7,806,139 | B2 | 10/2010 | Packham et al. |
| 7,815,614 | B2 | 10/2010 | Fangrow, Jr. |
| 7,837,658 | B2 | 11/2010 | Cote et al. |
| 7,857,805 | B2 | 12/2010 | Raines |
| 7,867,215 | B2 | 1/2011 | Akerlund et al. |
| 7,875,019 | B2 | 1/2011 | Barron et al. |
| D636,079 | S | 4/2011 | Leypold et al. |
| 7,976,532 | B2 | 7/2011 | Kitani et al. |
| 7,998,134 | B2 | 8/2011 | Fangrow et al. |
| 8,066,692 | B2 | 11/2011 | Simpson et al. |
| 8,113,546 | B2 | 2/2012 | Jensen et al. |
| 8,123,738 | B2 | 2/2012 | Vaillancourt |
| 8,162,013 | B2 | 4/2012 | Rosenquist et al. |
| 8,162,914 | B2 | 4/2012 | Kraushaar et al. |
| 8,177,760 | B2 | 5/2012 | Rome et al. |
| D662,122 | S | 6/2012 | Goodwin et al. |
| 8,196,606 | B2 | 6/2012 | Kitagawa |
| 8,196,614 | B2 | 6/2012 | Kriheli |
| 8,197,452 | B2 | 6/2012 | Harding et al. |
| 8,197,466 | B2 | 6/2012 | Yokota et al. |
| 8,211,069 | B2 | 7/2012 | Fangrow, Jr. |
| 8,225,826 | B2 | 7/2012 | Horppu et al. |
| 8,231,567 | B2 | 7/2012 | Tennican et al. |
| 8,235,426 | B2 | 8/2012 | Pisula, Jr. et al. |
| 8,251,346 | B2 | 8/2012 | Stroup |
| 8,262,628 | B2 | 9/2012 | Fangrow, Jr. |
| 8,277,424 | B2 | 10/2012 | Pan et al. |
| 8,281,824 | B2 | 10/2012 | Molema et al. |
| 8,286,936 | B2 | 10/2012 | Kitani et al. |
| 8,287,513 | B2 | 10/2012 | Ellstrom et al. |
| 8,287,518 | B2 | 10/2012 | Kitani et al. |
| 8,298,195 | B2 | 10/2012 | Peppel |
| 8,336,587 | B2 | 12/2012 | Rosenquist et al. |
| 8,337,483 | B2 | 12/2012 | Harding et al. |
| 8,361,408 | B2 | 1/2013 | Lynn |
| 8,366,676 | B2 | 2/2013 | Harding et al. |
| 8,372,059 | B2 | 2/2013 | Ziman |
| 8,377,010 | B2 | 2/2013 | Harding et al. |
| 8,392,756 | B2 | 3/2013 | Nakayama et al. |
| 8,397,756 | B2 | 3/2013 | Packham et al. |
| 8,403,894 | B2 | 3/2013 | Lynn et al. |
| 8,403,905 | B2 | 3/2013 | Yow |
| 8,408,226 | B2 | 4/2013 | Raines et al. |
| 8,409,165 | B2 | 4/2013 | Niedospial, Jr. et al. |
| 8,414,554 | B2 | 4/2013 | Garfield et al. |
| 8,414,555 | B2 | 4/2013 | Garfield et al. |
| 8,448,994 | B2 | 5/2013 | Pisula, Jr. et al. |
| 8,454,579 | B2 | 6/2013 | Fangrow, Jr. |
| 8,479,370 | B2 | 7/2013 | Grant |
| 8,500,717 | B2 | 8/2013 | Becker |
| 8,529,524 | B2 | 9/2013 | Newton et al. |
| 8,556,868 | B2 | 10/2013 | Simpson et al. |
| 8,596,688 | B2 | 12/2013 | Pisula, Jr. et al. |
| 8,603,047 | B2 | 12/2013 | Stroup |
| 8,628,516 | B2 | 1/2014 | Naftalovitz et al. |
| 8,641,685 | B2 | 2/2014 | Mansour et al. |
| 8,647,310 | B2 | 2/2014 | Fangrow, Jr. et al. |
| 8,667,997 | B2 | 3/2014 | Costanzo |
| 8,671,964 | B2 | 3/2014 | Py |
| 8,679,090 | B2 | 3/2014 | Anderson et al. |
| 8,684,994 | B2 | 4/2014 | Lev et al. |
| 8,702,675 | B2 | 4/2014 | Imai |
| 8,715,222 | B2 | 5/2014 | Truitt et al. |
| 8,715,247 | B2 | 5/2014 | Mansour et al. |
| 8,721,614 | B2 | 5/2014 | Takemoto et al. |
| 8,721,627 | B2 | 5/2014 | Albert |
| 8,721,628 | B2 | 5/2014 | Ziman |
| 8,746,278 | B2 | 6/2014 | Py |
| 8,764,731 | B2 | 7/2014 | Burgess et al. |
| 8,777,908 | B2 | 7/2014 | Fangrow, Jr. |
| 8,777,909 | B2 | 7/2014 | Fangrow, Jr. |
| 8,777,931 | B2 | 7/2014 | Davis et al. |
| 8,790,327 | B2 | 7/2014 | Takemoto |
| 8,790,330 | B2 | 7/2014 | Rosenquist |
| 8,795,256 | B1 | 8/2014 | Smith |
| 8,801,678 | B2 | 8/2014 | Panian et al. |
| 8,834,432 | B2 | 9/2014 | Winsor et al. |
| 8,864,725 | B2 | 10/2014 | Ranalletta et al. |
| 8,864,737 | B2 | 10/2014 | Hasegawa et al. |
| 8,870,832 | B2 | 10/2014 | Raday et al. |
| 8,870,846 | B2 | 10/2014 | Davis et al. |
| 8,876,784 | B2 | 11/2014 | Coete, Sr. et al. |
| 8,882,742 | B2 | 11/2014 | Dikeman et al. |
| 8,888,758 | B2 | 11/2014 | Mansour et al. |
| 8,899,267 | B2 | 12/2014 | Diodati et al. |
| 8,910,919 | B2 | 12/2014 | Bonnal et al. |
| 8,951,233 | B2 | 2/2015 | Mansour |
| 8,968,261 | B2 | 3/2015 | Kimball et al. |
| 8,968,271 | B2 | 3/2015 | Guala |
| 8,974,425 | B2 | 3/2015 | Tachizaki et al. |
| 8,979,804 | B2 | 3/2015 | Ho et al. |
| 9,017,295 | B2 | 4/2015 | Pan |
| 9,032,997 | B2 | 5/2015 | Abura et al. |
| 9,039,047 | B2 | 5/2015 | Imai |
| 9,044,554 | B2 | 6/2015 | Wu et al. |
| 9,044,585 | B2 | 6/2015 | Masuda et al. |
| 9,061,130 | B2 | 6/2015 | Truitt et al. |
| 9,067,049 | B2 | 6/2015 | Panian et al. |
| 9,089,680 | B2 | 7/2015 | Ueda et al. |
| 9,089,681 | B2 | 7/2015 | Ueda et al. |
| 9,114,242 | B2 | 8/2015 | Fangrow et al. |
| 9,114,244 | B2 | 8/2015 | Yeh et al. |
| 9,119,950 | B2 | 9/2015 | Mansour et al. |
| 9,126,028 | B2 | 9/2015 | Fangrow et al. |
| 9,126,029 | B2 | 9/2015 | Fangrow et al. |
| 9,138,572 | B2 | 9/2015 | Zeytoonian et al. |
| 9,149,622 | B2 | 10/2015 | Bonnet et al. |
| 9,168,203 | B2 | 10/2015 | Rosenquist et al. |
| 9,168,366 | B2 | 10/2015 | Fangrow et al. |
| 9,198,831 | B2 | 12/2015 | Rogers |
| 9,220,882 | B2 | 12/2015 | Belley et al. |
| 9,234,616 | B2 | 1/2016 | Carrez et al. |
| 9,238,128 | B2 | 1/2016 | Yamaguchi et al. |
| 9,308,317 | B2 | 4/2016 | Poncon |
| 9,314,604 | B2 | 4/2016 | Bonnal et al. |
| 9,345,641 | B2 | 5/2016 | Kraus et al. |
| 9,351,906 | B2 | 5/2016 | Garfield et al. |
| 9,358,182 | B2 | 6/2016 | Garfield et al. |
| 9,358,379 | B2 | 6/2016 | Fangrow |
| 9,393,398 | B2 | 7/2016 | Truitt et al. |
| 9,409,007 | B2 | 8/2016 | Yeh |

(56)　　　　　　References Cited

U.S. PATENT DOCUMENTS

| | | | |
|---|---|---|---|
| 9,433,768 | B2 | 9/2016 | Tekeste et al. |
| 9,541,227 | B2 | 1/2017 | Okiyama |
| 9,592,344 | B2 | 3/2017 | Simpson et al. |
| 9,636,492 | B2 | 5/2017 | Fangrow, Jr. |
| 9,683,683 | B2 | 6/2017 | Reuter |
| 9,707,346 | B2 | 7/2017 | Simpson et al. |
| D793,553 | S | 8/2017 | Stillson |
| 9,724,504 | B2 | 8/2017 | Fangrow, Jr. et al. |
| 9,726,308 | B2 | 8/2017 | Williams et al. |
| D799,938 | S | 10/2017 | Lowitz |
| D799,939 | S | 10/2017 | Lowitz |
| 9,775,979 | B2 | 10/2017 | Okiyama |
| 9,795,736 | B2 | 10/2017 | Okiyama |
| 9,814,870 | B2 | 11/2017 | Jin et al. |
| 9,833,605 | B2 | 12/2017 | Sanders et al. |
| 9,861,805 | B2 | 1/2018 | Dennis et al. |
| 9,884,177 | B2 | 2/2018 | Ueda et al. |
| 9,895,290 | B2 | 2/2018 | Cederschiöld et al. |
| 9,907,944 | B2 | 3/2018 | Liebe et al. |
| 9,913,945 | B2 | 3/2018 | Simpson et al. |
| 9,933,094 | B2 | 4/2018 | Fangrow |
| 9,950,152 | B2 | 4/2018 | Guala |
| 9,968,771 | B2 | 5/2018 | Wong |
| 9,974,939 | B2 | 5/2018 | Fangrow, Jr. |
| 9,974,940 | B2 | 5/2018 | Fangrow, Jr. |
| 9,987,407 | B2 | 6/2018 | Grant et al. |
| 9,993,634 | B2 | 6/2018 | Christensen et al. |
| 10,022,531 | B2 | 7/2018 | Shemesh |
| 10,046,154 | B2 | 8/2018 | Fangrow et al. |
| 10,098,816 | B2 | 10/2018 | Carney et al. |
| 10,105,492 | B2 | 10/2018 | Simpson |
| 10,149,940 | B2 | 12/2018 | Yagi et al. |
| 10,149,949 | B2 | 12/2018 | Tekeste et al. |
| 10,156,306 | B2 | 12/2018 | Fangrow |
| 10,188,847 | B2 | 1/2019 | Tohse et al. |
| 10,201,693 | B2 | 2/2019 | Tsai |
| 10,206,853 | B2 | 2/2019 | Sanders et al. |
| 10,207,096 | B2 | 2/2019 | Jensen et al. |
| 10,279,159 | B2 | 5/2019 | Andreen et al. |
| 10,279,160 | B2 | 5/2019 | Guala |
| 10,286,201 | B2 | 5/2019 | McKinnon et al. |
| D851,759 | S | 6/2019 | Jones et al. |
| 10,315,024 | B1 | 6/2019 | Vitello et al. |
| 10,357,643 | B2 | 7/2019 | Buchanan |
| 10,369,347 | B2 | 8/2019 | Lauer |
| D859,650 | S | 9/2019 | Steele et al. |
| 10,398,887 | B2 | 9/2019 | Fangrow, Jr. et al. |
| 10,473,246 | B2 | 11/2019 | Herrema et al. |
| D870,881 | S | 12/2019 | Mullani |
| 10,500,327 | B2 | 12/2019 | Grant et al. |
| 10,500,390 | B2 | 12/2019 | Ueda et al. |
| 10,500,391 | B2 | 12/2019 | Takeuchi |
| 10,518,076 | B2 | 12/2019 | Christie et al. |
| 10,518,077 | B2 | 12/2019 | Wong |
| 10,518,078 | B2 | 12/2019 | Stjernberg Bejhed et al. |
| 10,537,726 | B2 | 1/2020 | Guala |
| 10,556,099 | B2 | 2/2020 | Takeuchi |
| 10,569,073 | B2 | 2/2020 | Hallisey et al. |
| 10,569,074 | B2 | 2/2020 | Stenzel et al. |
| D879,956 | S | 3/2020 | Klenner et al. |
| 10,655,768 | B2 | 5/2020 | Jones et al. |
| 10,682,505 | B2 | 6/2020 | Shemesh |
| 10,682,506 | B2 | 6/2020 | Iwakata et al. |
| 10,695,549 | B2 | 6/2020 | Roxas et al. |
| 10,697,570 | B2 | 6/2020 | Fangrow |
| 10,716,928 | B2 | 7/2020 | Fangrow et al. |
| 10,744,317 | B2 | 8/2020 | Davis et al. |
| 10,842,982 | B2 | 11/2020 | Fangrow, Jr. |
| 10,842,983 | B2 | 11/2020 | De Ubaldi et al. |
| 10,850,086 | B2 | 12/2020 | Ueda et al. |
| 10,857,346 | B2 | 12/2020 | Dennis et al. |
| 10,864,362 | B2 | 12/2020 | Jones et al. |
| 11,168,818 | B2 | 11/2021 | Fangrow |
| 11,213,668 | B2 | 1/2022 | Mansour et al. |
| 11,266,785 | B2 | 3/2022 | Simpson et al. |
| 11,291,822 | B2 | 4/2022 | Jones et al. |
| 11,445,954 | B2 | 9/2022 | Jones et al. |
| 11,478,624 | B2 | 10/2022 | Fangrow et al. |
| 11,523,970 | B1 | 12/2022 | Vitello et al. |
| D976,982 | S | 1/2023 | Meyer |
| D982,140 | S | 3/2023 | Mitrovic |
| 11,648,383 | B2 | 5/2023 | Hallisey et al. |
| 11,701,040 | B2 | 7/2023 | Jones et al. |
| 11,708,924 | B2 | 7/2023 | Mansour et al. |
| 11,786,715 | B2 | 10/2023 | Fangrow, Jr. et al. |
| 11,808,389 | B2 | 11/2023 | Fangrow |
| 11,857,751 | B1 | 1/2024 | Vitello |
| D1,029,247 | S | 5/2024 | Janzen |
| D1,037,443 | S | 7/2024 | Kawachi |
| D1,038,388 | S | 8/2024 | Kawachi |
| D1,038,389 | S | 8/2024 | Kawachi |
| D1,038,390 | S | 8/2024 | Kawachi |
| D1,038,391 | S | 8/2024 | Kawachi |
| 12,072,049 | B2 | 8/2024 | Mansour et al. |
| D1,042,800 | S | 9/2024 | Sender et al. |
| D1,042,817 | S | 9/2024 | Fangrow |
| D1,042,822 | S | 9/2024 | Sender et al. |
| 12,076,522 | B2 | 9/2024 | Erekovcanski et al. |
| 12,109,387 | B2 | 10/2024 | Feith |
| 12,134,500 | B2 | 11/2024 | Wurm |
| D1,059,589 | S | 1/2025 | Reed et al. |
| D1,065,524 | S | 3/2025 | Kawachi |
| D1,069,110 | S | 4/2025 | Hund |
| D1,071,162 | S | 4/2025 | Neby |
| D1,071,169 | S | 4/2025 | Consolaro et al. |
| D1,071,202 | S | 4/2025 | Ubbesen |
| 12,280,230 | B2 | 4/2025 | Fangrow et al. |
| D1,073,939 | S | 5/2025 | Sender et al. |
| D1,075,002 | S | 5/2025 | Yang |
| D1,077,216 | S | 5/2025 | Kawachi |
| 12,320,453 | B2 | 6/2025 | Fangrow |
| D1,100,189 | S | 10/2025 | Fangrow |
| 2001/0029355 | A1 | 10/2001 | Szames et al. |
| 2001/0049490 | A1 | 12/2001 | Slanda et al. |
| 2002/0066715 | A1 | 6/2002 | Niedospial, Jr. |
| 2002/0153503 | A1 | 10/2002 | Newton et al. |
| 2003/0060804 | A1 | 3/2003 | Vaillancourt |
| 2003/0066978 | A1 | 4/2003 | Enerson |
| 2003/0111623 | A1 | 6/2003 | Enerson |
| 2003/0136932 | A1 | 7/2003 | Doyle |
| 2003/0151256 | A1 | 8/2003 | Guala |
| 2003/0201639 | A1 | 10/2003 | Korkor |
| 2003/0208165 | A1 | 11/2003 | Christensen et al. |
| 2004/0074541 | A1 | 4/2004 | Sharpe |
| 2004/0124388 | A1 | 7/2004 | Kiehne |
| 2004/0124389 | A1 | 7/2004 | Phillips |
| 2004/0238776 | A1 | 12/2004 | Peters et al. |
| 2004/0244848 | A1 | 12/2004 | Maldavs |
| 2005/0015075 | A1 | 1/2005 | Wright et al. |
| 2005/0033268 | A1 | 2/2005 | Decaria |
| 2005/0090805 | A1 | 4/2005 | Shaw et al. |
| 2005/0124942 | A1 | 6/2005 | Richmond |
| 2005/0212292 | A1 | 9/2005 | Parrino et al. |
| 2005/0228362 | A1 | 10/2005 | Vaillancourt |
| 2005/0245872 | A1 | 11/2005 | Simpson et al. |
| 2006/0025751 | A1 | 2/2006 | Roy et al. |
| 2006/0058734 | A1 | 3/2006 | Phillips |
| 2006/0129109 | A1 | 6/2006 | Shaw et al. |
| 2006/0142730 | A1 | 6/2006 | Proulx et al. |
| 2006/0149213 | A1 | 7/2006 | Raybuck |
| 2006/0157971 | A1 | 7/2006 | Baldwin et al. |
| 2006/0161115 | A1 | 7/2006 | Fangrow |
| 2006/0192164 | A1 | 8/2006 | Korogi et al. |
| 2006/0202146 | A1 | 9/2006 | Doyle |
| 2006/0211996 | A1 | 9/2006 | Trinchera et al. |
| 2006/0253084 | A1 | 11/2006 | Nordgren |
| 2007/0043334 | A1 | 2/2007 | Guala |
| 2007/0066965 | A1 | 3/2007 | Coambs et al. |
| 2007/0088292 | A1 | 4/2007 | Fangrow |
| 2007/0088293 | A1 | 4/2007 | Fangrow |
| 2007/0088294 | A1 | 4/2007 | Fangrow |
| 2007/0088327 | A1 | 4/2007 | Guala |
| 2007/0102923 | A1 | 5/2007 | Niemela |
| 2007/0179453 | A1 | 8/2007 | Lim et al. |

(56) References Cited

U.S. PATENT DOCUMENTS

| | | |
|---|---|---|
| 2007/0179454 A1 | 8/2007 | Ziman et al. |
| 2008/0103485 A1 | 5/2008 | Kruger |
| 2008/0125756 A1 | 5/2008 | Dicarlo et al. |
| 2008/0140020 A1 | 6/2008 | Shirley |
| 2008/0190485 A1 | 8/2008 | Guala |
| 2008/0200900 A1 | 8/2008 | Aeschlimann et al. |
| 2008/0290657 A1 | 11/2008 | McKeon, III |
| 2009/0001720 A1 | 1/2009 | Cheon et al. |
| 2010/0211019 A1 | 8/2010 | Greco |
| 2010/0249723 A1 | 9/2010 | Fangrow, Jr. |
| 2010/0253070 A1 | 10/2010 | Cheon et al. |
| 2010/0264343 A1 | 10/2010 | Jeory |
| 2010/0292673 A1 | 11/2010 | Korogi et al. |
| 2011/0046572 A1 | 2/2011 | Fangrow |
| 2011/0062703 A1 | 3/2011 | Lopez |
| 2011/0074148 A1 | 3/2011 | Imai |
| 2011/0175347 A1 | 7/2011 | Okiyama |
| 2011/0306931 A1 | 12/2011 | Kamen et al. |
| 2011/0319859 A1 | 12/2011 | Zeytoonian et al. |
| 2012/0031515 A1 | 2/2012 | Whitaker |
| 2012/0046636 A1 | 2/2012 | Kriheli |
| 2012/0089101 A1 | 4/2012 | Carlyon et al. |
| 2012/0109077 A1 | 5/2012 | Ryan |
| 2012/0153201 A1 | 6/2012 | Larose et al. |
| 2012/0220955 A1 | 8/2012 | Maseda et al. |
| 2012/0220984 A1 | 8/2012 | Christensen et al. |
| 2012/0271246 A1 | 10/2012 | Guala |
| 2012/0277688 A1 | 11/2012 | Rogier |
| 2012/0316536 A1 | 12/2012 | Carrez et al. |
| 2013/0006211 A1 | 1/2013 | Takemoto |
| 2013/0053815 A1 | 2/2013 | Mucientes et al. |
| 2013/0060205 A1 | 3/2013 | Mansour et al. |
| 2013/0076019 A1 | 3/2013 | Takemoto |
| 2013/0079730 A1 | 3/2013 | Mosler et al. |
| 2013/0197453 A1 | 8/2013 | Yeh |
| 2013/0317483 A1 | 11/2013 | Reichart et al. |
| 2014/0020792 A1 | 1/2014 | Kraus et al. |
| 2014/0174578 A1 | 6/2014 | Bonnal et al. |
| 2014/0246616 A1 | 9/2014 | Fangrow |
| 2014/0265319 A1 | 9/2014 | Clark et al. |
| 2014/0358033 A1 | 12/2014 | Lynn |
| 2014/0358073 A1 | 12/2014 | Panian et al. |
| 2014/0371686 A1 | 12/2014 | Sano et al. |
| 2015/0008664 A1 | 1/2015 | Tachizaki |
| 2015/0045746 A1 | 2/2015 | Macy, Jr. et al. |
| 2015/0073380 A1 | 3/2015 | Mansour et al. |
| 2015/0148756 A1 | 5/2015 | Lynn |
| 2015/0157848 A1 | 6/2015 | Wu et al. |
| 2015/0196749 A1 | 7/2015 | Ziv et al. |
| 2015/0202424 A1 | 7/2015 | Harton |
| 2015/0209233 A1 | 7/2015 | Fukuoka |
| 2015/0258324 A1 | 9/2015 | Chida et al. |
| 2015/0258325 A1 | 9/2015 | Panian et al. |
| 2015/0265829 A1 | 9/2015 | Truitt et al. |
| 2015/0320992 A1 | 11/2015 | Bonnet et al. |
| 2016/0030729 A1 | 2/2016 | McLean |
| 2016/0114147 A1 | 4/2016 | Siopes et al. |
| 2016/0144109 A1 | 5/2016 | Stroup |
| 2016/0158518 A1 | 6/2016 | Hallynck et al. |
| 2016/0250102 A1 | 9/2016 | Garfield et al. |
| 2016/0250415 A1* | 9/2016 | Yagi .................. A61M 39/1011 |
| | | 604/187 |
| 2016/0263369 A1 | 9/2016 | Naftalovitz et al. |
| 2016/0354288 A1 | 12/2016 | Uehara et al. |
| 2017/0191595 A1 | 7/2017 | Van Scyoc |
| 2017/0296801 A1 | 10/2017 | Fangrow, Jr. |
| 2017/0304547 A1 | 10/2017 | Simpson |
| 2018/0015275 A1 | 1/2018 | Fangrow, Jr. et al. |
| 2018/0036524 A1 | 2/2018 | Fangrow, Jr. |
| 2018/0085286 A1 | 3/2018 | Kim et al. |
| 2018/0133451 A1 | 5/2018 | Takeuchi |
| 2018/0172190 A1 | 6/2018 | Fangrow |
| 2018/0193566 A1 | 7/2018 | Simpson |
| 2018/0207418 A1 | 7/2018 | Ueda |
| 2018/0214683 A1 | 8/2018 | Ueda |
| 2018/0289920 A1 | 10/2018 | Harding et al. |
| 2018/0303720 A1 | 10/2018 | Kennard et al. |
| 2018/0339146 A1 | 11/2018 | Schrauder et al. |
| 2019/0053980 A1 | 2/2019 | West et al. |
| 2019/0076319 A1 | 3/2019 | Okiyama |
| 2019/0078712 A1 | 3/2019 | Fangrow |
| 2019/0224468 A1 | 7/2019 | Jones |
| 2019/0247642 A1 | 8/2019 | Karthikeyan et al. |
| 2019/0275314 A1 | 9/2019 | Jeffrey |
| 2019/0282794 A1 | 9/2019 | Carlsson et al. |
| 2019/0321564 A1 | 10/2019 | Kim et al. |
| 2020/0000979 A1 | 1/2020 | Myers |
| 2020/0016391 A1 | 1/2020 | Di Ubaldi |
| 2020/0094036 A1 | 3/2020 | Wong |
| 2020/0101237 A1 | 4/2020 | Biggers et al. |
| 2020/0114139 A1 | 4/2020 | Mills et al. |
| 2020/0271171 A1 | 8/2020 | Leung |
| 2020/0316361 A1 | 10/2020 | Kakinoki et al. |
| 2020/0316362 A1 | 10/2020 | Jeffrey |
| 2020/0345996 A1 | 11/2020 | DeMeritt et al. |
| 2020/0384256 A1 | 12/2020 | Hopkinson |
| 2021/0252267 A1 | 8/2021 | Fangrow, Jr. |
| 2021/0283343 A1 | 9/2021 | Mills et al. |
| 2021/0372551 A1 | 12/2021 | Clark et al. |
| 2022/0008294 A1 | 1/2022 | Sanders et al. |
| 2022/0288378 A1 | 9/2022 | Mermelshtein et al. |
| 2022/0296869 A1 | 9/2022 | Jones et al. |
| 2022/0370697 A1 | 11/2022 | Parikh et al. |
| 2023/0001172 A1 | 1/2023 | Wine et al. |
| 2023/0040378 A1 | 2/2023 | Jones et al. |
| 2023/0059045 A1 | 2/2023 | Feith et al. |
| 2023/0139756 A1 | 5/2023 | Wine et al. |
| 2023/0149689 A1 | 5/2023 | Armstrong et al. |
| 2023/0302268 A1 | 9/2023 | Fangrow |
| 2023/0321425 A1 | 10/2023 | Jadhav et al. |
| 2023/0355946 A1 | 11/2023 | Kuriyama |
| 2023/0372691 A1 | 11/2023 | Kuriyama et al. |
| 2024/0011588 A1 | 1/2024 | Fangrow |
| 2024/0024652 A1 | 1/2024 | Fangrow, Jr. |
| 2024/0042188 A1 | 2/2024 | Wine et al. |
| 2024/0050728 A1 | 2/2024 | Jadhav et al. |
| 2024/0151338 A1 | 5/2024 | Desai et al. |
| 2024/0157110 A1 | 5/2024 | Shafiq et al. |
| 2024/0157112 A1 | 5/2024 | Feith et al. |
| 2024/0167602 A1 | 5/2024 | Wine |
| 2024/0173531 A1 | 5/2024 | Kumar et al. |
| 2024/0173537 A1 | 5/2024 | Nalawade et al. |
| 2024/0204452 A1 | 6/2024 | Wine |
| 2024/0207594 A1 | 6/2024 | Jadhav et al. |
| 2024/0238578 A1 | 7/2024 | Wine et al. |
| 2024/0245898 A1 | 7/2024 | Malviya et al. |
| 2024/0261555 A1 | 8/2024 | Nelson et al. |
| 2024/0269452 A1 | 8/2024 | Wells et al. |
| 2024/0293657 A1 | 9/2024 | Kuriyama |
| 2024/0316330 A1 | 9/2024 | Kumar et al. |
| 2024/0325715 A1 | 10/2024 | Cai et al. |
| 2024/0328553 A1 | 10/2024 | Austin et al. |
| 2024/0328555 A1 | 10/2024 | Austin et al. |
| 2024/0358988 A1 | 10/2024 | Gaffney et al. |
| 2024/0358989 A1 | 10/2024 | Gaffney et al. |
| 2024/0377007 A1 | 11/2024 | Kakaraparthi et al. |
| 2025/0018165 A1 | 1/2025 | Callahan et al. |
| 2025/0032769 A1 | 1/2025 | Callahan et al. |
| 2025/0114587 A1 | 4/2025 | Wells |
| 2025/0161649 A1 | 5/2025 | Fangrow |
| 2025/0172226 A1 | 5/2025 | Fangrow |

FOREIGN PATENT DOCUMENTS

| | | |
|---|---|---|
| EP | 0 158 030 | 10/1985 |
| EP | 0 368 473 | 5/1990 |
| EP | 0 791 371 | 8/1997 |
| EP | 0 795 342 | 9/1997 |
| EP | 1 050 318 | 11/2000 |
| EP | 1 904 152 | 4/2008 |
| EP | 1 917 996 | 5/2008 |
| EP | 1 946 792 | 7/2008 |
| EP | 2 123 322 | 11/2009 |
| EP | 3 381 502 | 10/2018 |

(56) References Cited

FOREIGN PATENT DOCUMENTS

| EP | 3 884 990 | | 9/2021 |
|----|-----------|---|--------|
| GB | 2 116 277 | | 9/1983 |
| GB | 2 118 440 | | 11/1983 |
| GB | 2 353 078 | | 2/2001 |
| JP | 56-72659 | U1 | 6/1981 |
| JP | 58-13216 | | 1/1983 |
| JP | 59-41429 | | 3/1984 |
| JP | 60-89488 | | 6/1985 |
| JP | 62-65779 | | 4/1987 |
| JP | 63-175383 | | 11/1988 |
| JP | 11-311234 | | 11/1999 |
| JP | 2001-187990 | A | 7/2001 |
| JP | 2003-192100 | | 7/2003 |
| JP | 2004-000483 | A | 1/2004 |
| WO | WO 1988/08499 | | 11/1988 |
| WO | WO 1995/32748 | | 12/1995 |
| WO | WO 1996/33762 | | 10/1996 |
| WO | WO 1998/22178 | | 5/1998 |
| WO | WO 2001/03756 | | 1/2001 |
| WO | WO 2001/23026 | | 4/2001 |
| WO | WO 2002/066100 | | 8/2002 |
| WO | WO 2002/096500 | | 12/2002 |
| WO | WO 2004/060474 | | 7/2004 |
| WO | WO 2004/082756 | | 9/2004 |
| WO | WO 2006/076656 | | 7/2006 |
| WO | WO 2006/088858 | | 8/2006 |
| WO | WO 2006/124756 | | 11/2006 |
| WO | WO 2009/095760 | | 8/2009 |
| WO | WO 2013/036854 | | 3/2013 |
| WO | WO 2015/065958 | | 5/2015 |
| WO | WO 2023/014720 | | 2/2023 |
| WO | WO 2023/018737 | | 2/2023 |
| WO | WO 2023/193007 | | 10/2023 |
| WO | WO 2024/100671 | | 5/2024 |
| WO | WO 2024/108047 | | 5/2024 |
| WO | WO 2025/076278 | | 4/2025 |

OTHER PUBLICATIONS

Assignee websited, products/pharmacy preparations/closed system transfer devices/chemolock,product literature—oncology intravesical administration, Jan. 1, 2021, https://www.icumed.com/media/ Ofqhrnkl/p23-6036-2-intravesical-administration-brochure-v2.pdf (Year: 2021).

Injection Site, Molded Products, Inc., Apr. 2, 2004, in 1 page, https://web.archive.org/web/20040402123354/https://www.moldedproducts.com/injectionsite.htm.

International Search Report for PCT/US2006/026124, dated Mar. 3, 2007 in 5 pgs.

International Written Opinion for PCT/US2006/026124, dated Jan. 10, 2008 in 11 pgs.

International Search Report and Written Opinion of International Application No. PCT/US2008/063797 mailed on Dec. 30, 2008 in 21 pages.

International Preliminary Report on Patentability, International Application No. PCT/US2008/063797 mailed on Nov. 17, 2009 in 11 pages.

International Search Report and Written Opinion re PCT App. No. PCT/US2009/068857, dated (mailed) Apr. 8, 2010.

International Preliminary Report on Patentability re PCT App. No. PCT/US2009/068857, issued, Jun. 21, 2011 in 8 pages.

International Search Report and Written Opinion re PCT App. No. PCT/US2011/034854, mailed Mar. 28, 2012.

International Preliminary Report on Patentability re PCT App. No. PCT/US2011/034854, issued Nov. 6, 2012, 2012.

International Search Report and Written Opinion for International Application No. PCT/US2004/042723, issued on Jun. 28, 2005 in 16 pages.

International Written Opinion of International Application No. PCT/US2004/042723 issued on Jul. 3, 2006 in 10 pages.

International Search Report and Written Opinion re PCT Application No. PCT/US2012/054289, mailed Jan. 24, 2013.

International Preliminary Report on Patentability and Written Opinion re PCT Application No. PCT/US2012/054289, mailed Mar. 12, 2014.

International Search Report and Written Opinion, re PCT Application No. PCT/US2022/039183, mailed Oct. 28, 2022.

International Search Report and Written Opinion, re PCT Application No. PCT/US2023/080155, mailed Mar. 20, 2024.

International Search Report and Written Opinion, re PCT Application No. PCT/US2023/065237, mailed Sep. 25, 2023.

International Search Report and Written Opinion, re PCT Application No. PCT/US2024/049865, mailed Jan. 7, 2025.

International Preliminary Report on Patentability, re PCT Application No. PCT/US2023/080155, issued Apr. 29, 2025.

* cited by examiner

300

304

302

320

328

312

310

308

330

314

302

306

318

300

324

326

316

304

MEDICAL CONNECTORS

CROSS-REFERENCE TO RELATED APPLICATIONS

This application claims the benefit under 35 U.S.C. § 119(e) of U.S. Provisional Patent Application No. 63/228,982, filed Aug. 3, 2021, and titled MEDICAL CONNECTORS. The entirety contents of each of the above-identified application(s) are hereby incorporated by reference herein and made part of this specification for all that they disclose.

BACKGROUND

Field of the Disclosure

Some embodiments disclosed herein relate to medical connectors.

Description of the Related Art

Although various medical connectors exist there remains a need for improved medical connectors.

SUMMARY

Certain example embodiments are summarized below for illustrative purposes. The embodiments are not limited to the specific implementations recited herein. Embodiments may include several novel features, no single one of which is solely responsible for its desirable attributes or which is essential to the embodiments.

Various embodiments disclosed herein can relate to a medical connector, which can include a proximal end with a proximal opening, a distal end with a distal opening, and a fluid pathway between the proximal end and the distal end. The connector can include a body portion and a projection extending distally from the body portion with a proximal step formed between the body portion and the projection. The projection can include a distal step. The projection can include a male luer with a tapered outer surface configured to engage a tapered inner surface of a female luer. A collar can be disposed between the proximal step and the distal step. The collar can substantially surround the projection. The collar can have internal threading. An adapter can include a proximal portion having one or more projections that extend inward and engage the distal step on the projection to couple the adapter to the projection. The adapter can have a distal portion having internal threading.

The proximal portion of the adapter can be between the projection and the collar. The proximal portion of the adapter can fit inside of the collar without engaging the threading of the collar. The one or more projections can include an annular flange. The adapter can include one or more arms, which can be configured to apply a force when manipulated that displaces the one or more projections to facilitate disengagement of the adapter from the projection. The proximal portion of the adapter can include one or more slits. The medical connector can include a seal element between the adapter and the projection. The seal element can include an O-ring or a gasket. The adapter can include a shroud that extends proximally to substantially cover the body portion.

Various embodiments disclosed herein can relate to an adapter, which can be configured to couple a first medical connector to a second medical connector. The adapter can include a proximal portion configured to enable linear coupling of the first medical connector to the adapter without rotation of the adapter relative to the first medical connector. The adapter can include a distal portion configured to enable rotational coupling of the second medical connector to the adapter.

The proximal portion can include one or more projections that extend inward and are configured to engage an engagement feature on the first medical connector. The one or more projections can include an annular flange. The proximal portion can have an outer diameter that is smaller than an outer diameter of the distal portion. The adapter can include one or more arms, which can be configured to apply a force when manipulated to widen the proximal portion to facilitate disengagement of the adapter from the first medical connector. The proximal portion can include one or more slits. The adapter can include a seal element disposed on an inside of the adapter. The seal element can include an O-ring or a gasket. The adapter can include a shroud that extends proximally past the proximal portion.

Various embodiments disclosed herein can relate to an adapter, which can be configured to couple a first medical connector to a second medical connector. The adapter can include a proximal portion that can include one or more snap-fit engagement features for linearly engaging the first medical connector. The adapter can include a distal portion that comprises internal threading for rotationally engaging the second medical connector.

The proximal portion can have an outer diameter that is smaller than an outer diameter of the distal portion. The adapter can include one or more arms, which can be configured to apply a force when manipulated to widen the proximal portion to facilitate disengagement of the adapter from the first medical connector. The proximal portion can include one or more slits. The adapter can include a seal element disposed on an inside of the adapter. The seal element can include an O-ring or a gasket. The adapter can include a shroud that extends proximally past the proximal portion. The one or more snap-fit engagement features can include a proximal sliding surface, and a distal engagement surface.

Various embodiments disclosed herein can relate to a medical connector, which can include a distal end with a distal opening and a proximal end with a proximal opening. The proximal end can include a female luer bore and external threading. The medical connector can have a fluid pathway between the proximal end and the distal end. An adapter can include a distal portion having internal threading that engages the external threading of the proximal end. The adapter can include a proximal portion, which can have one or more projections with a proximal angled sliding surface and a distal engagement surface. The proximal portion of the adapter can have an outer diameter that is smaller than an outer diameter of the distal portion of the adapter. The one or more projections can provide snap-fit engagement features. The proximal portion of the adapter can be configured to linearly engage another connector.

Various embodiments disclosed herein can relate to a method, which can include accessing a first medical connector, which can include a proximal end with a proximal opening, a distal end with a distal opening, a fluid pathway between the proximal end and the distal end, a body portion, and a projection extending distally from the body portion. The projection can include a step. The projection can include a male luer with a tapered outer surface that can be configured to engage a tapered inner surface of a female luer. The first medical connector can include a collar substantially surrounding the projection. The collar can have internal threading. The method can include accessing an adapter that can include a proximal portion having one or more projections that extend inward and a distal portion having internal threading. The method can include coupling the adapter to the first medical connector by inserting the projection into the proximal portion of the adapter and advancing the adapter axially in a proximal direction until the one or more projections engage the step on the projection.

The proximal portion of the adapter can be inserted into the collar as the adapter is advanced axially. The method can include accessing a second medical connector that can include a distal end with a distal opening and a proximal end with a proximal opening. The proximal end can include a female luer and external threading. The second medical connector can include a fluid pathway can be between the proximal end and the distal end. The method can include coupling the second medical connector to the adapter by inserting the proximal end of the second medical connector into the distal portion of the adapter and rotating the second medical connector relative to the adapter so that the external threading on the proximal end of the second medical connector engages the internal threading on the distal portion of the adapter so that the male luer of first medical connector sealingly engages the female luer of the second medical connector. The method can include rotating the second medical connector relative to the adapter further so that one or more breakable elements on the second medical connector break to transition the second medical connector to a free-spin configuration.

Various embodiments disclosed herein can relate to a method, which can include accessing a first medical connector that can include a distal end with a distal opening and a proximal end with a proximal opening. The proximal end can include a female luer and external threading. The first medical connector can have a fluid pathway between the proximal end and the distal end. The first medical connector can have an adapter, which can include a distal portion having internal threading that engages the external threading of the proximal end and a proximal portion having one or more protrusions. The method can include accessing a second medical connector that can include a proximal end with a proximal opening, a distal end with a distal opening, a fluid pathway between the proximal end and the distal end, a body portion, and a projection extending distally from the body portion. The projection can include a step. The projection can include a male luer with a tapered outer surface. The second medical connector can include a collar substantially surrounding the projection. The collar can include internal threading. The method can include coupling the second medical connector to the adapter by inserting the projection into the proximal portion of the adapter and advancing the adapter axially in a proximal direction with respect to the second connector until the one or more protrusions engage the step on the projection, and so that the male luer of second medical connector sealingly engages the female luer of the first medical connector.

BRIEF DESCRIPTION OF THE DRAWINGS

Certain embodiments will be discussed in detail with reference to the following figures, wherein like reference numerals refer to similar features throughout. These figures are provided for illustrative purposes and the embodiments are not limited to the specific implementations illustrated in the figures.

DETAILED DESCRIPTION OF CERTAIN EMBODIMENTS

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/ or substituted as will be apparent to those of ordinary skill in the art upon consideration of the principles disclosed herein.

Figure 1:
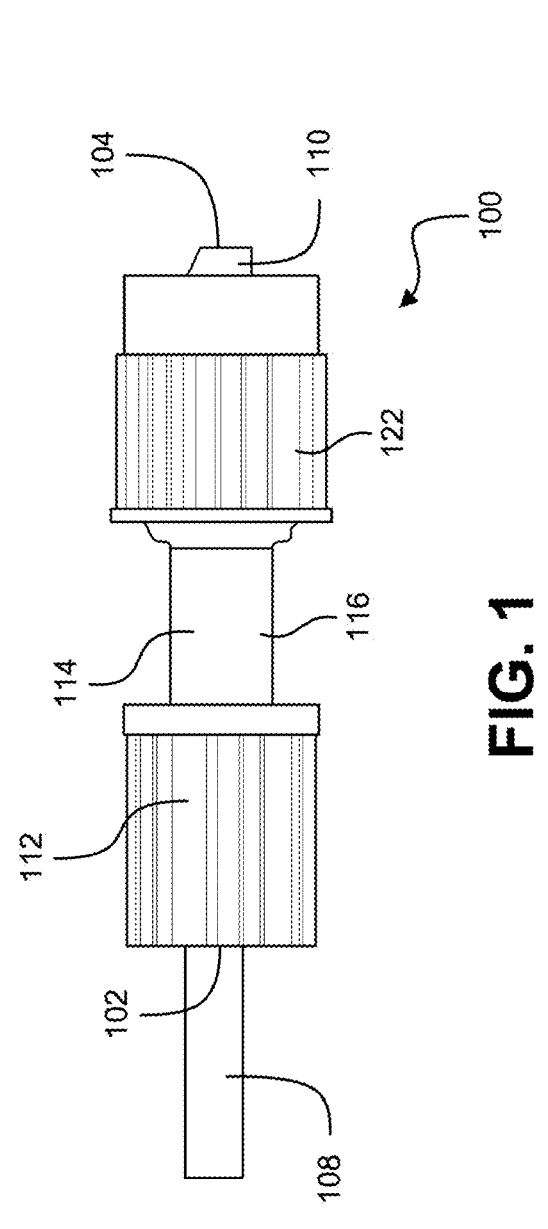
FIG. 1 shows an example embodiment of a medical connector.
Figure 2:
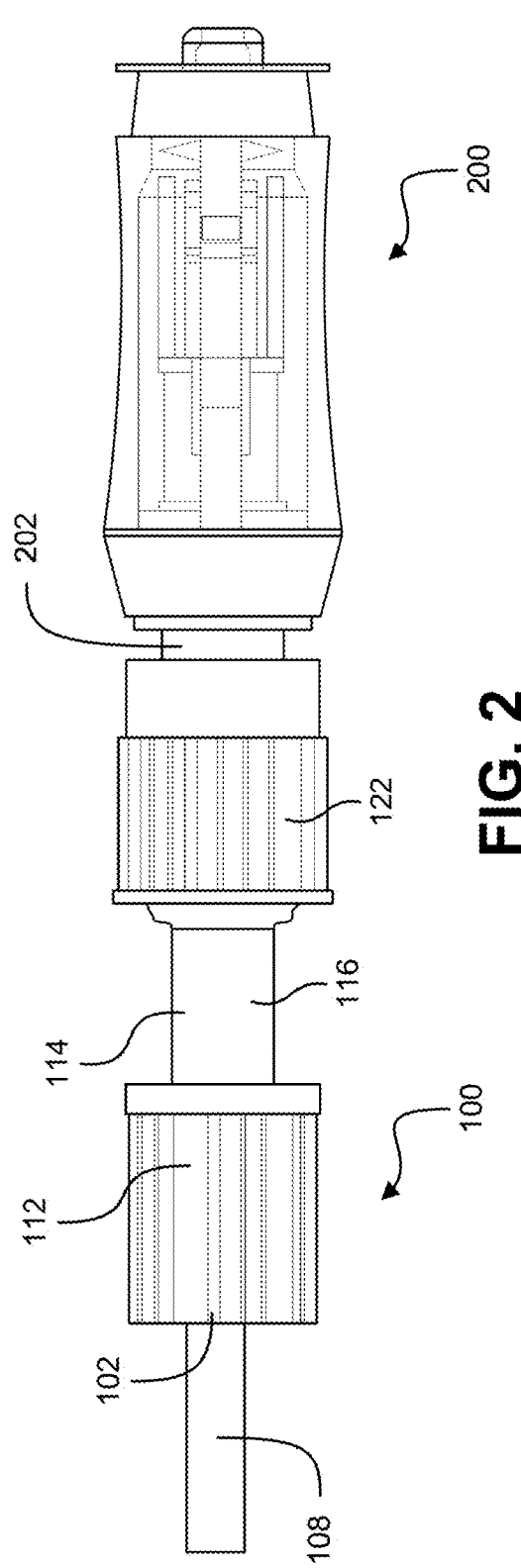
FIG. 2 shows the medical connector of FIG. 1 coupled to another medical connector.
Figure 3:
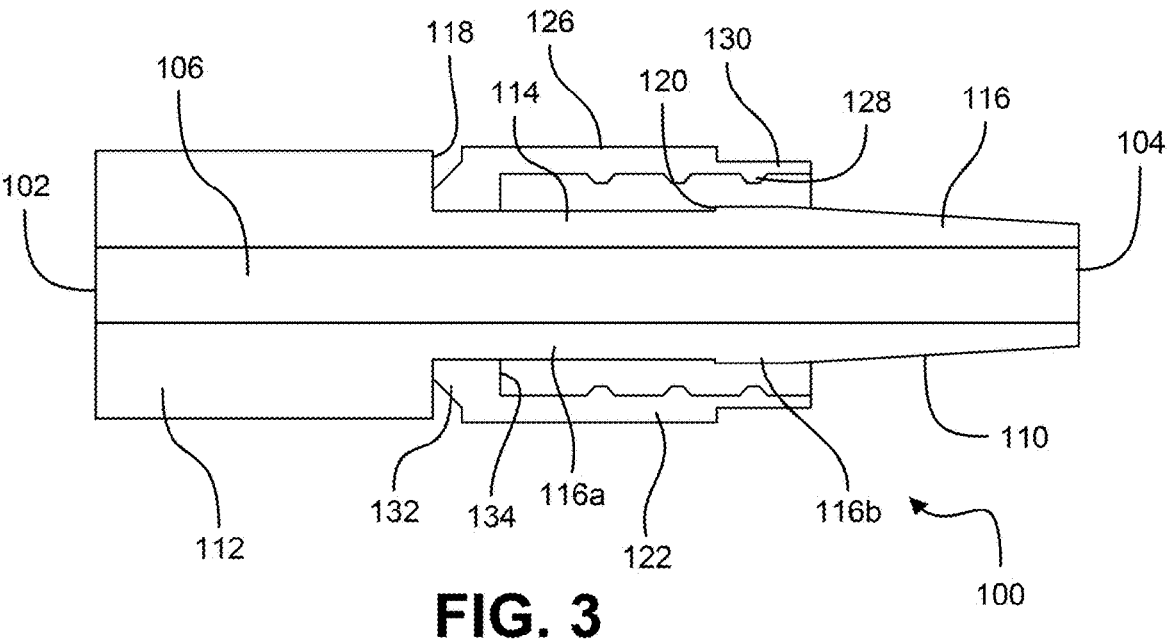
FIG. 3 is a cross-sectional view of the connector of FIG. 1.
Figure 4:
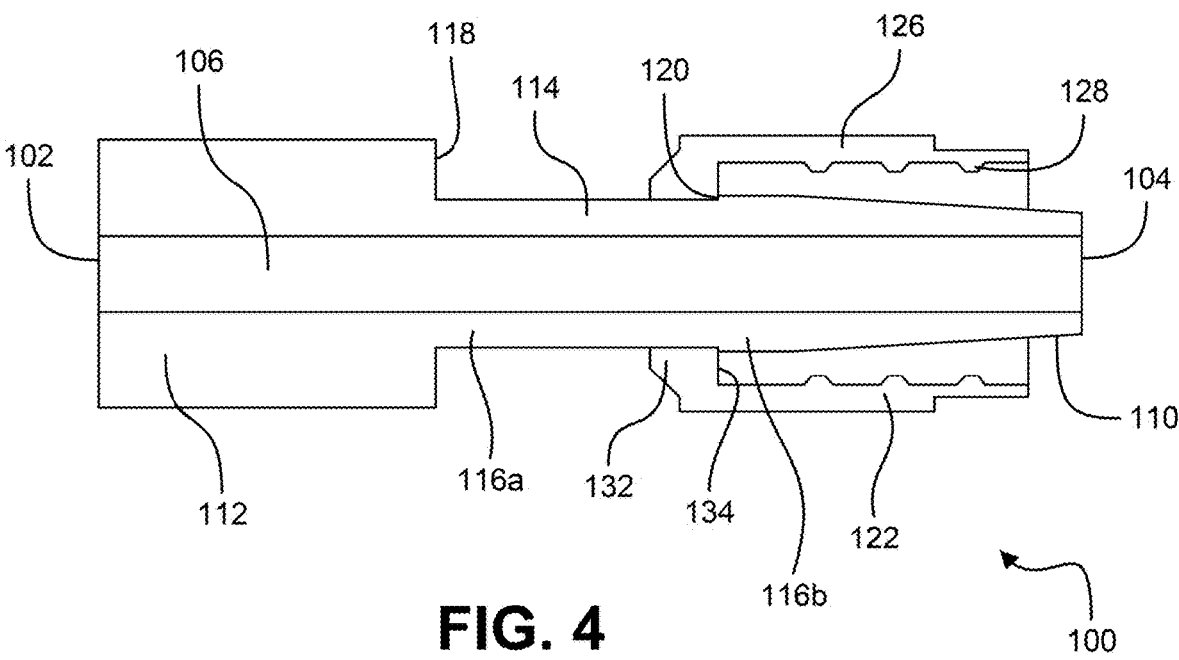
FIG. 4 is another cross-sectional view of the connector of FIG. 1.

FIG. 1 shows an example medical connector 100. FIG. 2 shows the medical connector 100 coupled to another medical connector 200. FIGS. 3 and 4 show cross-sectional views of the connector 100. The medical connector 100 can have a proximal end 102 with a proximal opening, and a distal end 104 with a distal opening. A fluid pathway 106 fluidically couples the proximal opening to the distal opening. In some cases, the fluid pathway can be a linear fluid pathway without turns or obstructions, and the fluid pathway can have a substantially uniform inner diameter, although various other configurations could be used. The proximal end 102 can be coupled to a conduit 108, such as flexible medical tubing or a catheter, so that the conduit is in fluid communication with the fluid pathway 106 through the connector 100. The conduit 108 can be coupled to the connector 100 by an adhesive, a friction fitment, sonic welding, or any other suitable engagement. The proximal end 102 of the connector 100 can be coupled to various other medical implements capable of transporting fluid, such as a syringe, another connector, a pump, etc. In some implementations, the proximal end 102 can have engagement features for removable coupling with a medical implement (e.g., a female luer, or other coupling structure). In some implementations, the conduit 108 can couple the connector 100 to a pump, medical fluid bag, other fluid source, or other medical implement. The distal portion of the connector 100 can have a male connection feature, such as a male luer 110, which can be an ANSI-compliant male luer tip. The male luer 110 can have a tapered outer surface, which can be configured to engage with corresponding tapered inner surface of a female luer, which can be an ANSI-compliant female luer.

The connector 100 can include a body portion 112. The outer surface of the body portion 112 can have texture, protrusions, recesses, splines, and/or other gripping features configured to facilitate gripping of the body portion by the user during some operations, such as during the process of connecting or disconnecting the connector 100 to another medical implement. A projection 114 can extend distally from the body portion 112. The distal end of the projection 114 can include the male luer 110. An extension portion 116 of the projection 114 can extend between the body portion 112 and the male luer 110. The projection 114 (e.g., the extension portion 116) can have an outer diameter or cross-sectional area that is smaller than the outer diameter or cross-sectional area of the body portion 112, so that a step 118 is formed at the transition between the body portion 112 and the projection 114. The step 118 can be at the distal end of the body portion 112 and/or at the proximal end of the projection 114. In some implementations, the extension portion 116 can have an outer surface that does not include a tapered surface (e.g., not having an ANSI-compliant tapered surface). The extension portion 116 can have one or more sections with substantially uniform outer diameter(s). As can be seen in FIGS. 3 and 4, a first section 116a of the extension portion can have a first outer diameter, and a second section 116b of the extension portion can have a second outer diameter that is larger than the first outer diameter, so that a step 120 is formed at the transition from the first section 116a to the second section 116b. The second section 116b can be positioned distally from the first section 116a. In some cases, the second section 116b of the extension portion can be omitted, so that the tapered surface of the male luer 110 starts at the step 120. In some variations, the step 120 can be formed by a protrusion, such as an annular protrusion.

The connector 100 can include a collar 122, which can include a shroud 124, which can have one or more sidewalls 126 that at least partially surrounds a recess. The collar 122 can have a continuous, annular sidewall 126, although the sidewall 126 can have breaks, or slits, or separated portions or fingers. The inside of the sidewall 126 can have threading 128, which can be configured to engage corresponding threading on a medical implement, such as the connector 200 shown in FIG. 2. The outer surface of the side wall 126 can have texture, protrusions, recesses, splines, and/or other gripping features configured to facilitate gripping of the collar 122 by the user during some operations, such as during the process of connecting or disconnecting the connector 100 to another medical implement. In some implementations, the collar 122 can have a distal portion 130 that does not have the gripping features. The portion of the collar 122 with the gripping features (e.g., splines) can have a larger outer diameter than the distal portion 130 of the collar 122 that does not have the gripping features (e.g., splines), which can form one or more steps (e.g., each individual spline can have a step at its distal end at the transition to the distal portion 130 of the collar 122.

The collar 122 can have an engagement portion 132 that engages the projection 114. The engagement portion 132 can have an opening with an inner diameter that is generally the same size as, or slightly larger than, the outer diameter of the projection 114 (e.g., the first section 116a of the protrusion). For example a flange can extend inward from the proximal end of the sidewall 126. An opening through the proximal end of the collar 122 can have a diameter that is smaller than a diameter of the recess formed by the sidewall 126, forming a step 134. The step 134 can be formed by the flange at a proximal portion of the collar (e.g., at the proximal end of the recess). The distal end of the collar 122 can be open to the recess.

The collar 122 can be movable relative to the body portion 112 and/or relative to the projection 114. FIG. 3 shows the collar 122 at a proximal position, where the proximal end of the collar 122 can abut against the step 118 or surface at the distal end of the body portion 112, to impede the collar 122 from moving further proximally. FIG. 4 shows the collar 122 at a distal position, where the step 134 abuts against the step 120 to impede the collar 122 from moving further distally. The range of motion for the collar 122 can be defined by the distance between the step 118 and the step 120 minus the distance between the step 134 and the proximal end of the collar 122. The collar 122 can be configured to move axially between the proximal and distal positions. The collar 122 can be configured to rotate (e.g., about a longitudinal axis that extends through the connector 100 between the proximal and distal ends, such as through the fluid path 106).

Figure 5:
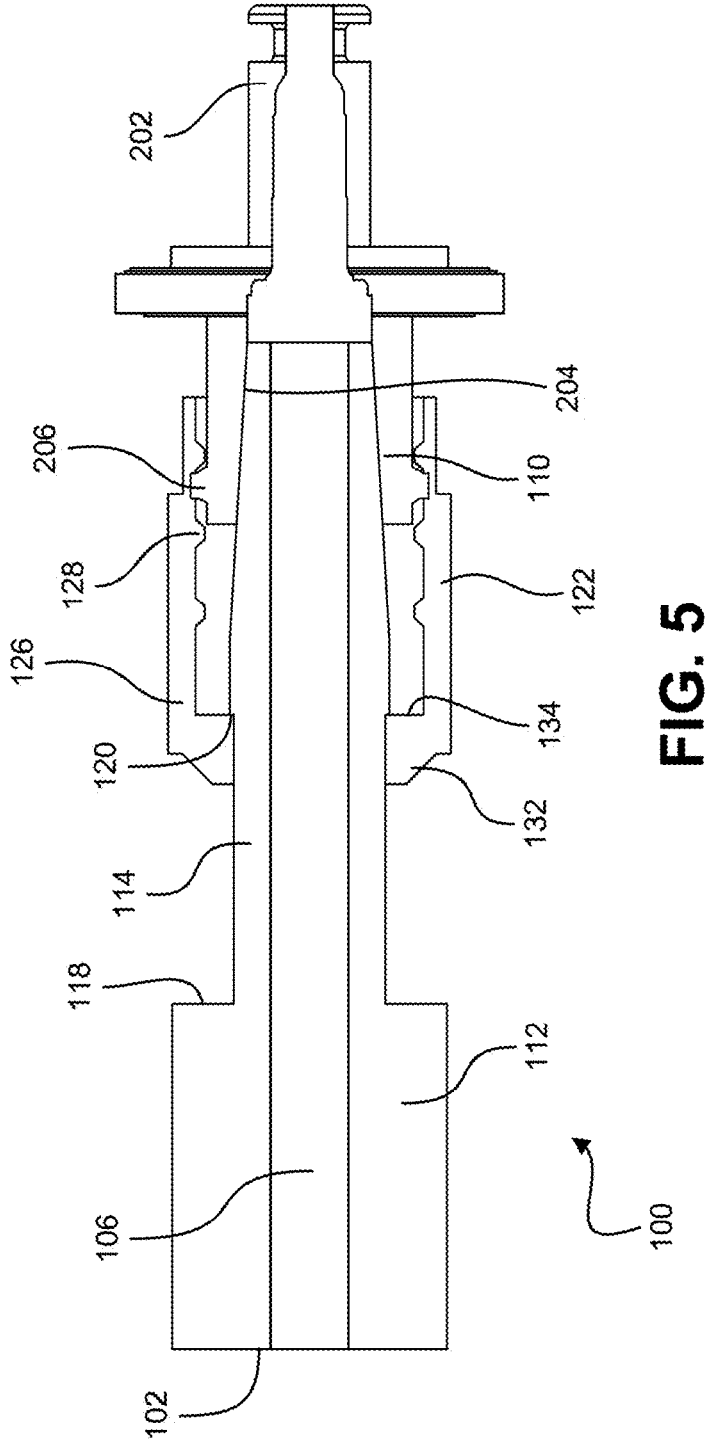
FIG. 5 is a cross-sectional view of an example embodiment of a first connector coupled to a portion of a second connector.

As shown in FIG. 2, the distal portion of the connector 100 can connect with a proximal portion 202 of a medical connector 200, or other medical implement. FIG. 5 shows a cross-sectional view of the connector 100 coupled to the proximal portion 202, with the rest of the connector 200 omitted from view. By way of example, the medical connector 200 have features similar to the connector embodiments disclosed in U.S. Patent Application Publication No. 2019/0078712 (the "'712 Publication"), published Mar. 14, 2019, and titled AXIALLY ENGAGING MEDICAL CONNECTOR SYSTEM WITH DIMINISHED FLUID REMNANTS, which is hereby incorporated by reference in its entirety. The connector proximal portion 202 that is shown in FIG. 5 can have features similar to the first cap component in the closable male connector embodiments disclosed in connection with FIGS. 1-20C of the '712 Publication. The proximal portion 202 can have a female luer 204, which can have a tapered surface that corresponds to the tapered surface of the male luer 110. The male luer 110 can advance distally to engage the female luer 204 so that the tapered surfaces form a seal the permit fluid to be transferred between the connectors 100, 200 substantially without leaking, during normal operation. Thus, the male luer 110 of the connector 100 can couple with a female luer of the connector 200. The exterior of the proximal portion 202 can have threading 206, which can be configured to engage the threading 128 on the collar 122. The threading can include protrusions and/or grooves, and in some cases one side can have one or more spiral grooves and the other side can have one or more corresponding spiral protrusions, or one or more protrusions that are not spiral-shaped but still engage the spiral groove(s). The collar 122 can be rotated onto the proximal portion 202 of the connector 200 so that the threading engagement advances the collar 122 distally towards the connector 200. The step 134 on the collar can press on the step 120 to advance the projection 114 (e.g., the male luer 110) distally as well.

During normal operation, the collar 122 advances the male luer 110 distally until the tapered surface of the male luer 110 substantially seals against the tapered surface of the female luer 204. However, in some cases, the collar 122 can be impeded from advancing distally, so that the male luer 110 does not properly engage with the female luer 204, which can cause the connection between the connectors 100, 200 to leak. For example, if the collar 122 is malformed (e.g., either during manufacturing or assembly) the collar 122 can bind as it is threaded onto the proximal portion 202. In some instances, the collar 122 can have an inner diameter that is smaller than the appropriate size to engage the proximal portion 202, such as due to manufacturing tolerances or defects. Various other features on the collar 122 can be misshaped to impede the collar 122 from advancing properly, such as the width, height, or pitch of the threading 128 inside the collar 122. In some cases, the engagement portion 132 of the collar 122 can be deformed during assembly, which can cause the collar 122 to be misaligned (e.g., when the step 134 abuts the step 120). These issues can increase the friction between the collar 122 and the proximal portion 202 and can impede the collar 122 from advancing distally, thereby resulting in leakage. The leakage can result in loss of fluid (e.g., which can be a costly drug), incorrect dosage or sampling volumes, and exposure to hazardous substances (e.g., chemotherapy drugs). A misshaped proximal portion 202 (e.g., a larger outer diameter, or threading 206 that is malformed) can also impede the collar 122 from advancing, which can cause leakage. Also, leakage can result from trying to attach the connector 100 to a device that is not designed to receive the collar 122, even if both components are properly formed.

In some implementations, the connector 200 can be configured to transition to a spinning configuration when a threshold amount of torque is applied to the connector 200. For example, as discussed in the '712 Publication, the connector can have one or more tabs that are configured to break when a threshold amount of torque is applied to the connector 200, and the proximal portion 202 can be configured to rotate relative to the rest of the connector 200 when the tabs are broken. Thus, a user can apply torque to twist the collar 122 and connector 200 together until the threshold torque is reached, at which point the tabs break so that the connector 200 merely spins when additional torque is applied. These features can be used to prevent the connector 200 from later being detached from the connector 100. This configuration can effectively set a maximum torque that can be applied when threading the collar 122 onto the connector 200. If that maximum torque is reached before the male luer 100 fully engages the female luer 204 to form a substantially fluid-tight seal (e.g., due to a misshapen collar 122), then the connection between the connectors 100, 200 may leak. When attaching the connector 100 to devices that do not have a maximum torque threshold, the user may be able to compensate for a misshaped collar by overtightening the collar 122 to advance the male luer 100 sufficiently to impede leakage. But for connectors 200 that have a torque-limiting feature, the same malformation in the collar 122 can result in leakage because the torque-limiting feature can be prevent the user from over overtightening the collar 122. Also, overtightening the collar 122 can lead to other problems, such as breaking or deforming the collar 112 or other components, which can result in significant leakage.

Figure 6A:
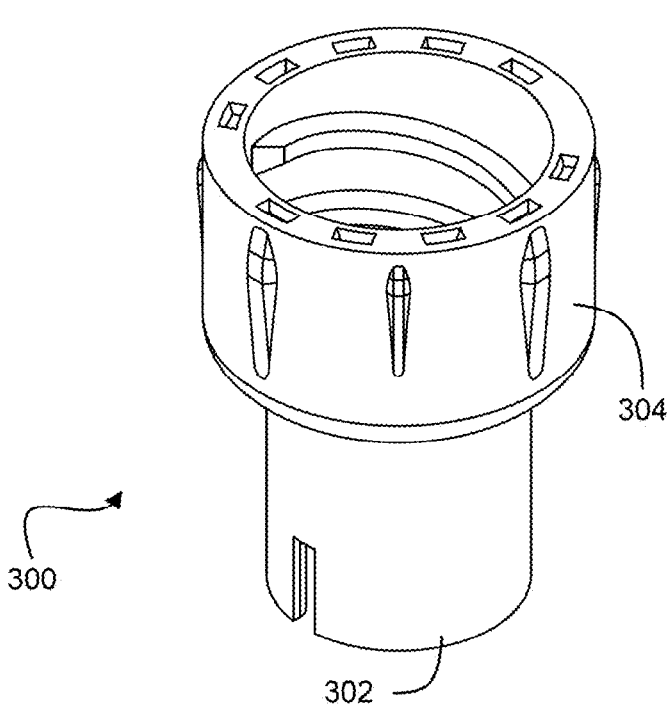
FIG. 6A shows a perspective view of an example embodiment of an adapter.
Figure 6B:
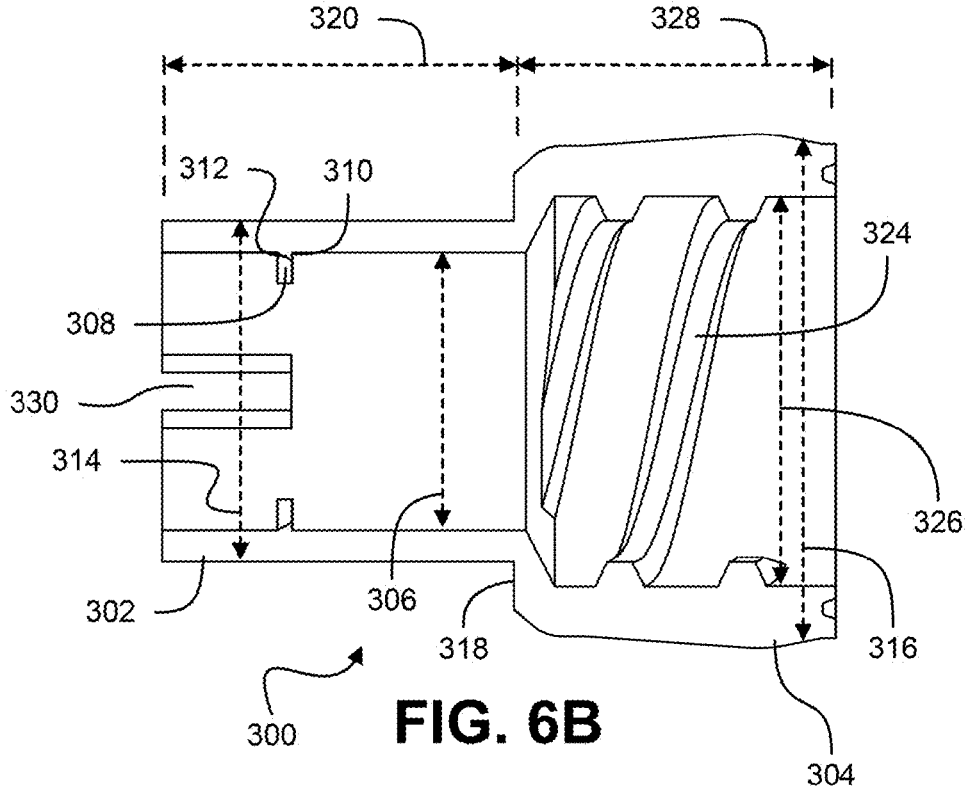
FIG. 6B is a cross-sectional view of the adapter of FIG. 6A.
Figure 6C:
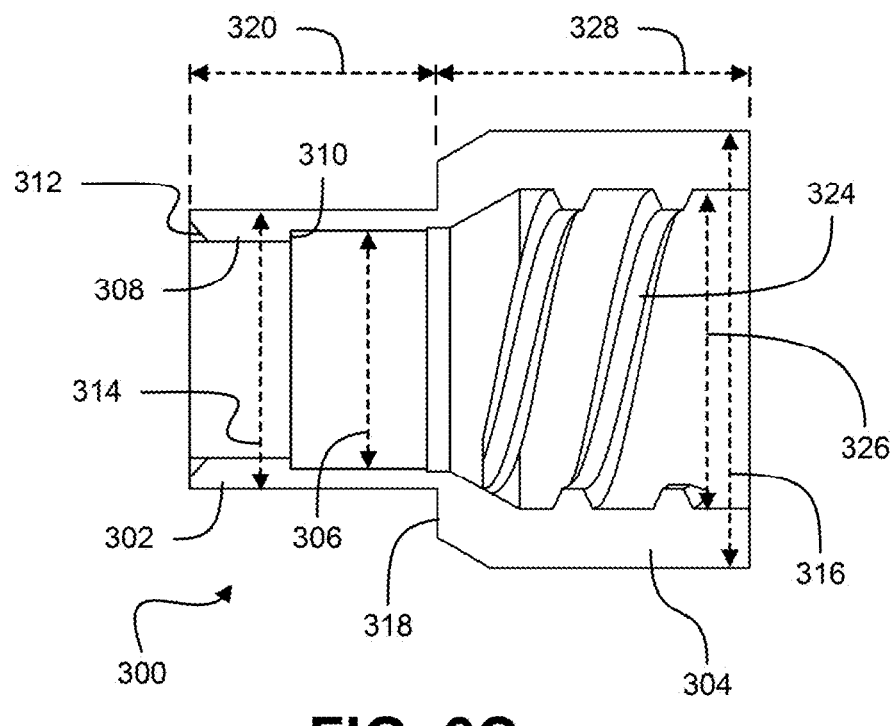
FIG. 6C is a cross-sectional view of another example embodiment of an adapter.
Figure 7:
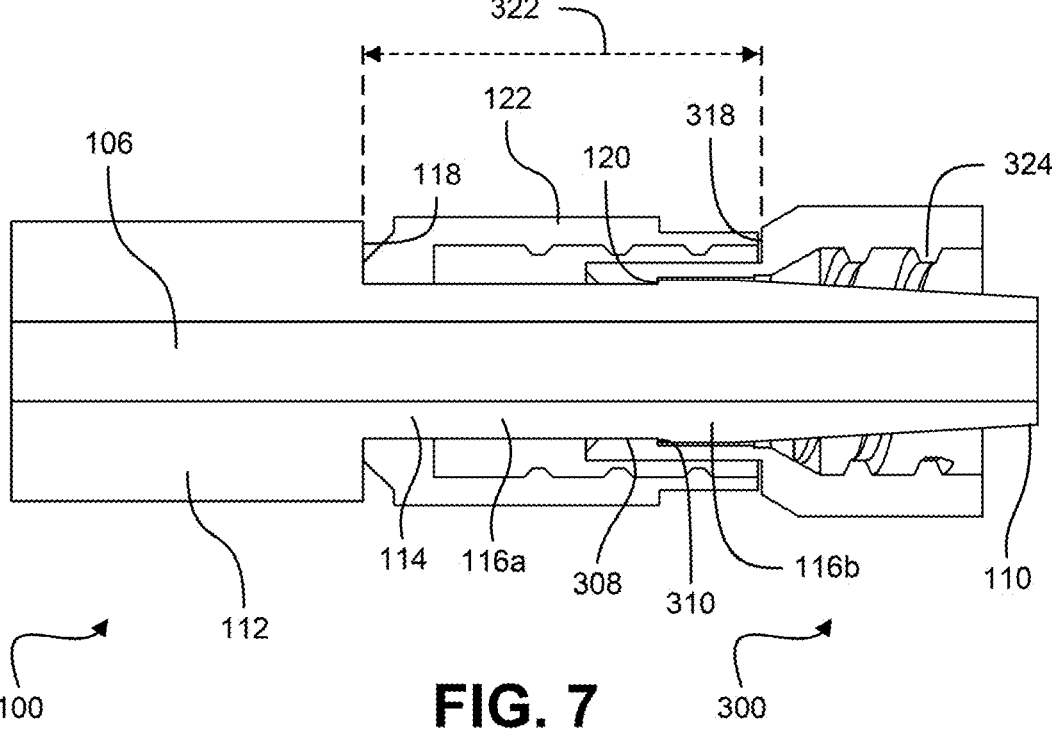
FIG. 7 is a cross-sectional view of the adapter of FIG. 6C coupled to a first connector
Figure 7A:
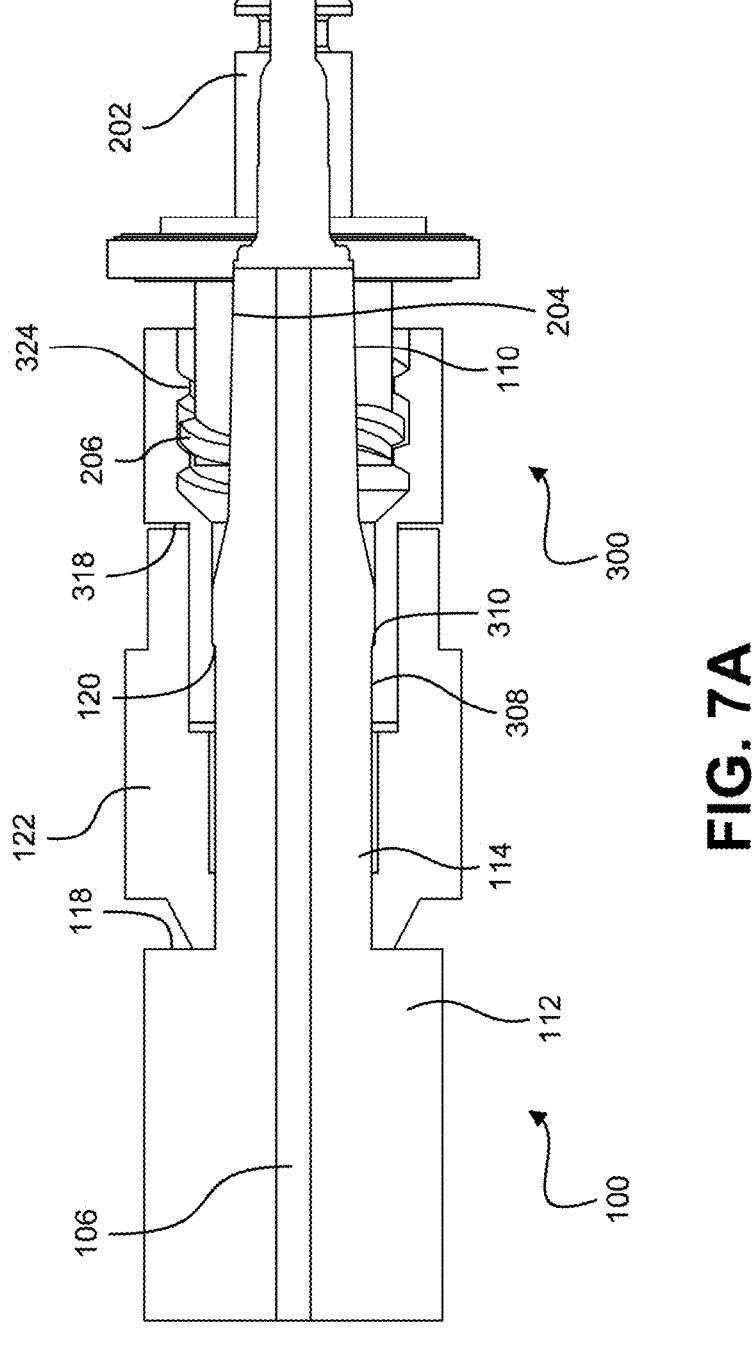
FIG. 7A is a cross-sectional view of an example embodiment of an adapter coupled to a first connector and to a component of a second connector.
Figure 7B:
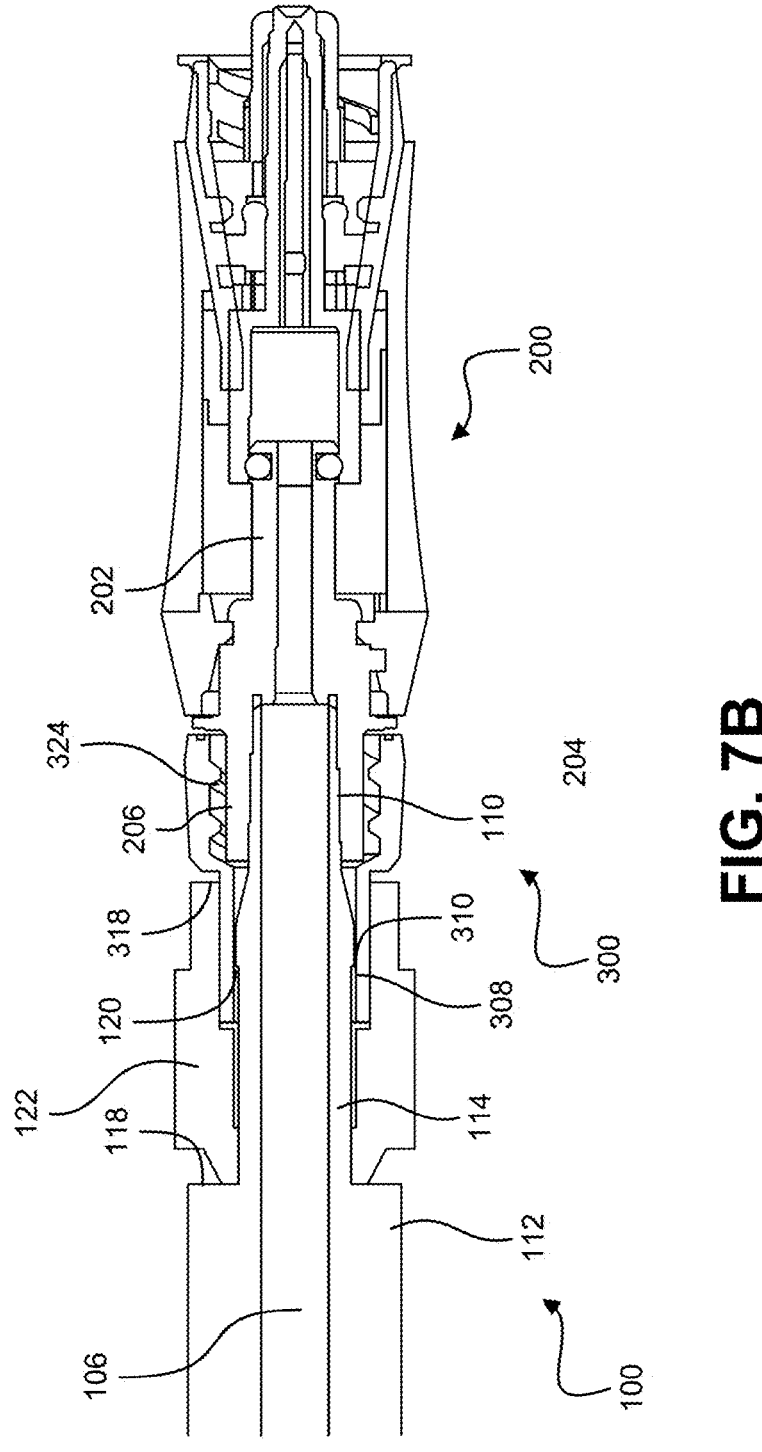
FIG. 7B is a cross-sectional view of an example embodiment of an adapter coupled between a first connector and a second connector.
Figure 7C:
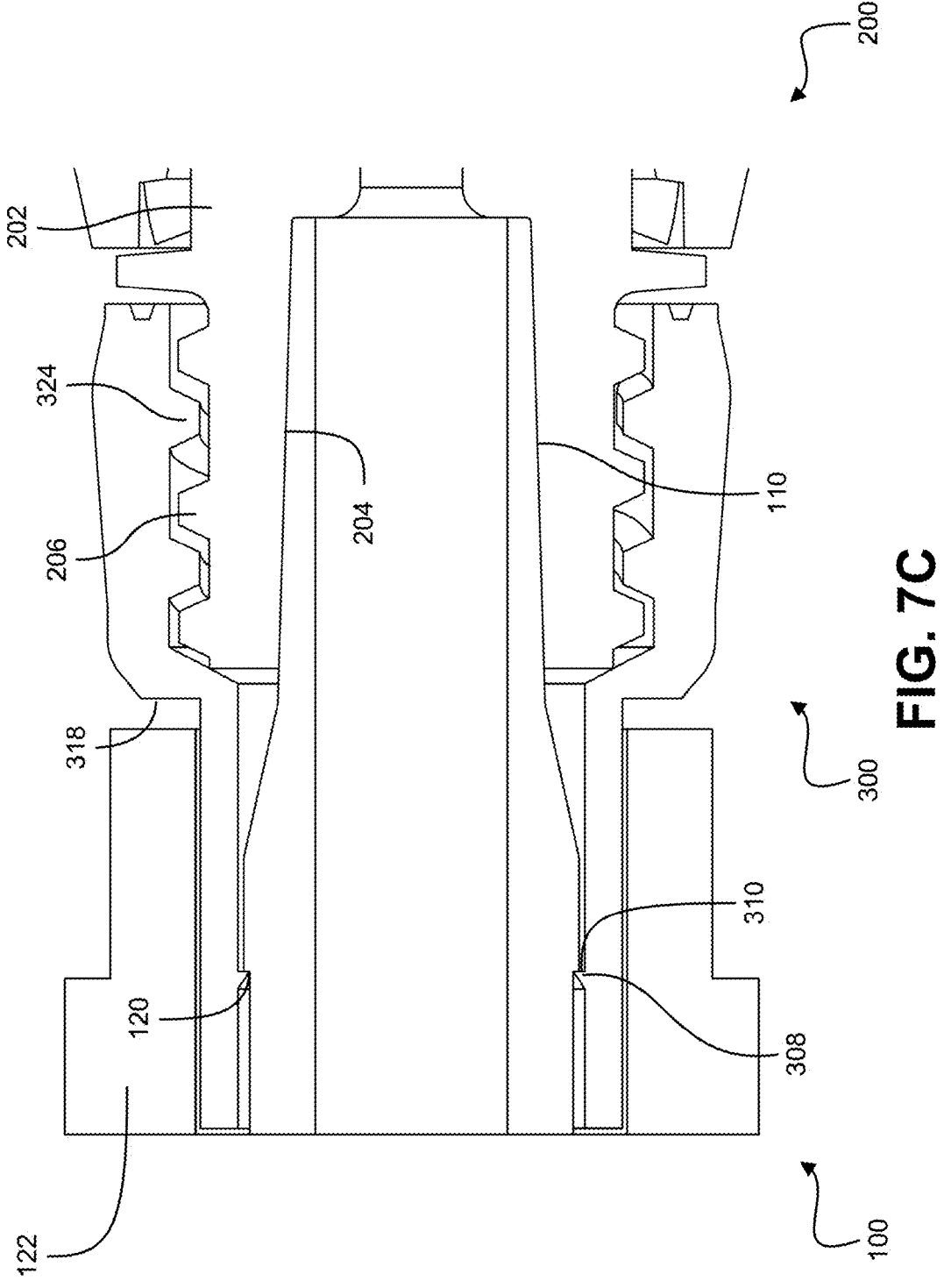
FIG. 7C is a detailed cross-sectional view of the engagement between the adapter with the first and second connectors.

In some embodiments, an adapter 300 can be used to couple the connector 100 to the connector 200, or to another medical implement. FIG. 6A shows a perspective view of an example embodiment of the adapter 300. FIG. 6B shows a cross-sectional view of the adapter 300 of FIG. 6A. FIG. 6C shows a cross-sectional view of another example embodiment of the adapter 300. FIG. 7A shows an example embodiment with the adapter 300 of FIG. 6C coupled to the connector 100 and a component of the connector 200. FIG. 7B shows a cross-sectional view of the adapter 300 coupled between the connector 100 and to the connector 200. FIG. 7C shows a detailed cross-sectional view of the engagement between the adapter 300 with the connectors 100, 200. The adapter 300 can be configured to have a snap-fit engagement with the connector 100 and a threaded engagement with the connector 200. In some embodiments, the adapter 300 can be used instead of the collar 122 of the connector 100. In some embodiments, when the adapter 300 is used to couple the connector 100 to the connector 200, the collar 122 does not engage the connector 200. The adapter 300 can displace the collar 122 of the connector 100 away from the connector 200.

The adapter 300 can have the general shape of a hollow cylinder with an annular sidewall that surrounds an open interior chamber, which can be open at the proximal and distal ends. The adapter 300 can include a proximal portion 302 and a distal portion 304. The proximal portion 302 can be configured to engage the connector 100, such as using a snap-fit engagement. The proximal portion 302 has an inner diameter 306, which can be substantially the same as, or larger than, the outer diameter of the projection 114 (e.g., the second section 116b of the protrusion), so that the distal portion 304 of the adapter 300 can fit onto the projection 114. The proximal portion 302 can include a flange 308, or one or more protrusions, which can extend inwardly, to form a step 310 or engagement surface. The flange 308 or protrusion(s) can form an area with an inner diameter that is generally the same size as, or slightly larger than, the outer diameter of the projection 114 (e.g., the first section 116a of the protrusion), and which inner diameter can be smaller than the inner diameter 306 of the proximal portion before the flange 308. The flange 308 or each of the protrusion(s) can define a step 310 or engagement surface. The flange 308 or one or more protrusion(s) is not threading, and can have substantially the same axial position around its circumference. As shown in FIG. 6C, the proximal end of the adapter 300 can have a tapered surface 312, which can be angled distally in the direction pointing radially inward. In some embodiments, the flange 308 or protrusions can include one or more teeth with angled sliding surfaces 312 on a side opposite the steps 310 or engagement surfaces, as shown in FIG. 6B, for example. In some embodiments, the flange 308 can extend substantially around the circumference of the inside of the adapter, as shown in FIG. 6C. In some embodiments, the one or more protrusions 308 can include distinct teeth or other protrusions that can be space around the inside of the adapter 300, as shown in FIG. 6B, for example.

To attach the adapter 300 to the connector 100, the projection 114 (e.g., the male luer 110) can be inserted through the proximal end of the adapter 300, and the adapter 300 can be moved axially in the proximal direction relative to the connector 100. The inner diameter at the flange 308 can be smaller than the outer diameter of the second portion 116b of the projection 114. The projection 114 (e.g., the second portion 116b thereof) can contact the flange 308 or protrusion(s), and as the adapter 300 moves further proximally, the flange 308 or protrusion(s) can flex, compress, or otherwise deform laterally outward. When the adapter 300 moves proximally enough for the flange 308 to clear the step 120, the flange 308 or protrusion(s) can move or expand laterally inward so that the proximal portion 302 of the adapter 300 is engaged with the projection 114 on the connector 100. In some implementations, the flange 308 or protrusion(s) can snap into place proximally of the step 120. The step 310 on the adapter 300 can abut against the step 120 on the connector 100 to impede the adapter from moving distally past the position shown in FIG. 7. The tapered surface 312 of the adapter can facilitate sliding of the adapter 300 over the projection 114 of the connector 100. The inner edge of proximal end can be beveled, rounded, or tapered to impede the inner edge from catching on the projection 114. When engaged with the connector 100, the adapter 300 can rotate (e.g., about a longitudinal axis).

The proximal portion 302 of the adapter 300 can have an outer diameter 314, which can be smaller than the inner diameter of the collar 122 on the connector 100, and/or can be smaller than the distance between opposing threads inside the collar 122, so that the proximal portion 302 of the adapter 300 can fit into the recess between the collar 122 and the projection 114. The adapter does not engage the threading 128 of the collar, so that the collar 122 and the adapter 300 can rotate relative to each other. The distal portion 304 of the adapter 300 can have an outer diameter 316 that is larger than the outer diameter 314 of the proximal portion 302, which can form a step 318 at the transition from the proximal portion 302 to the distal portion 304. The step 318 can push the collar 122 of the connector 100 proximally as the adapter 300 is coupled to the connector 100. The proximal portion 302 of the adapter 300 can have a length 320 (e.g., measured axially) that is sufficiently long so that when the proximal portion 302 of the adapter is engaged with the connector 100 (e.g., with the step 310 abutted against the step 120), the distance 322 between the step 318 and the step 118 at the distal end of the body portion 112 of the connector 100 is at least as long as the length of the collar 122 (e.g., measured axially between the portions that abut the step 118 and the step 318), and in some embodiments the distance 322 can be larger than the length of the collar 122 so that gap(s) can be formed between the collar 122 and the step 118 and/or between the collar 122 and the step 318. The collar 122 can have an axial range of motion between the step 118 and the step 318. In some embodiments the gap(s)

and/or axial range of motion can be less than about 10 mm, less than about 8 mm, less than about 6 mm, less than about 4 mm, less than about 2 mm, less than about 1 mm, or less, or any ranges or values between these listed values, although some implementations could use other dimensions. In some embodiments, the collar 122 can move to provide the same axial range of motion to the adapter 300. The collar 122 can axially fill the distance 322 between the steps 118, 318 by more than about 70%, by more than about 80%, by more than about 85%, by more than about 90%, by more than about 95%, by more than about 98%, or by about 100%, or any values or ranges between these listed values, although some implementations could use other dimensions.

The distal portion 304 can be configured to engage the connector 200, such as using a threaded engagement. FIG. 7 shows an example embodiment of an adapter 300 coupling the connector 100 to the connector 200 (only the proximal portion 202 of the connector 200 is visible in FIG. 7). The inside of the distal portion 304 of the adapter 300 can have threading 324. The exterior of the proximal portion 202 can have threading 206, which can be configured to engage the threading 324 on the adapter 300. The threading can include protrusions and/or grooves, and in some cases one side can have one or more spiral grooves and the other side can have one or more corresponding spiral protrusions, or one or more protrusions that are not spiral-shaped but still engage the spiral groove(s). The distal portion 304 of the adapter 300 can have an inner diameter 326, which can be large enough to receive the sidewall of the female luer 204 into the recess between the male luer 110 and the sidewall of the distal portion 304 of the adapter 300. The inner diameter 326 of the distal portion 304 can be larger than the inner diameter 306 of the proximal portion 302. The inner diameter 326 of the distal portion 304 can be larger than the outer diameter 314 of the proximal portion 302. The distal portion 304 can have a length (e.g., along an axial direction) that can be longer than, shorter than, or the same as the length 320 of the proximal portion.

In some embodiments, the adapter 300 can be attached first onto the connector 100 and then attached to the connector 200. As discussed herein, the adapter 300 can be pressed proximally onto the connector 100 until the adapter 300 engages the connector 100 (e.g., with a snap-fitting) to impede removal of the adapter 300 form the connector 100. The adapter 300 can push the collar 122 distally as the adapter 300 attaches to the connector 100. The proximal portion 302 of the adapter can insert into the recess between the projection 114 and the collar 122. The distal portion 304 of the adapter 300 can then be advanced distally so that the threading 324 engages the threading 206 on the proximal portion 202 of the connector 200. The adapter can be rotated relative to the connector 200, which can cause the adapter 300 to advance further distally. As the adapter 300 advances distally, the step 310 presses on the step 120 to advance the male luer 100 distally as well, until the outer tapered surface of the male luer 110 engages the inner tapered surface of the female luer 204, which can provide a substantially fluid-tight seal. The proximal portion 302 of the adapter 300 can be configured to linearly engage the first connector 100 (e.g., without rotating the adapter 300 relative to the first connector 100), and/or the distal portion 304 of the adapter 300 can be configured to rotationally engage the second connector 200.

In some embodiments, the adapter 300 can be attached first to the connector 200 and then attached to the connector 100. The distal portion 304 of the adapter can be threaded onto the proximal portion 202 of the connector 200. With no male luer 110 attached to the adapter 300, the adapter 300 could be threaded to a position expected to provide the sealing engagement (or perhaps to a position slightly proximal of that location). The male luer 110 can then be advanced through the adapter 300 and into the proximal portion 202. The male luer 110 and the rest of the projection can be advances distally (e.g. with no rotation needed) until the flange 308 or protrusion(s) engages (e.g., snaps into engagement with) the step 120. In some instances, the adapter 300 can be tightened to seal the male luer 110 against the female luer 204. In some instances, if the adapter 300 was advance distally too far to permit engagement with the connector 100, then the adapter 300 can be unthreaded to move the adapter proximally, which can enable the adapter to engage with the connector 100 (e.g., by snapping into place).

The connector 100 with the adapter 300 can have two nested collars. When the adapter 300 couples the connector 100 to the connector 200, the proximal portion 202 of the connector 200 can be positioned inside the distal portion 304 of the adapter, the proximal portion 302 of the adapter 300 can be positioned inside the distal portion of the collar 122, and/or the projection 114 of the connector can extend through the proximal portion of the collar 122, through the distal portion of collar 122, through the proximal portion 302 of the adapter 300, through the distal portion 304 of the adapter 300, and into the proximal portion 202 of the connector 200.

In some embodiments, the adapter 300 can be made from polycarbonate. In some embodiments, the collar 122 can be made from acrylic. Other suitable materials can be used for the adapter 300 and/or the collar 122 (as well as other components disclosed herein), including polymers, plastics, metals, glass, etc. In some embodiments, the adapter 300 can be made from a material that is harder than the material of the collar 122. The materials and the geometry can be configured to permit the adapter 300 to slide over the step 120 without the deforming or damaging the step 120 or the adapter 300 (e.g., the flange or protrusion(s) 308) in a way that impedes retention of the adapter 300 onto the connector 100. This can be achieved by the sizing of the components, flexibility of the geometry, flexibility of the materials of construction, or any combination thereof.

Figure 8:
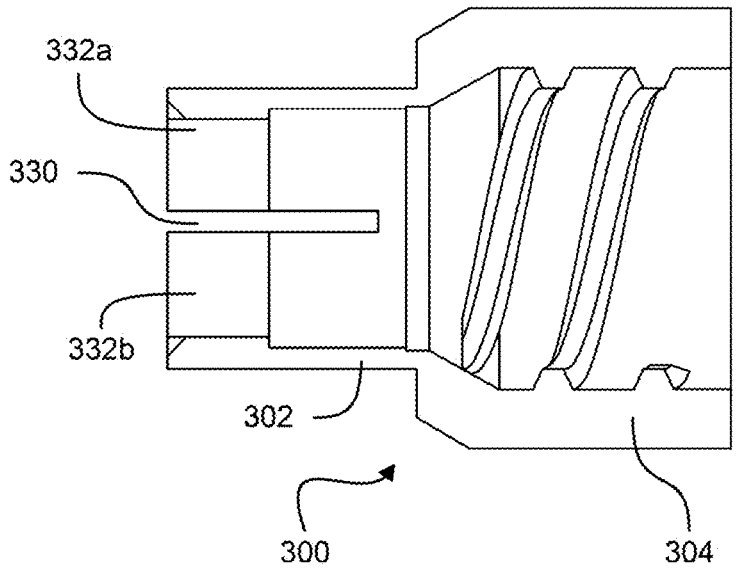
FIG. 8 is a cross-sectional view of an example embodiment of an adapter.

FIG. 8 shows a cross-sectional view of an example embodiment of an adapter 300. The adapter 300 can have a proximal portion 302 with one or more slits 330, which can facilitate flexing of the proximal portion 302 as the adapter 300 is being coupled onto the connector 100. In some cases, multiple slits 330 can be used, which can separate the proximal portion 302 into two or more sections. The embodiments of FIG. 6B also includes a slit 330. The proximal portion 302 can have two or more separated arms. For example, FIG. 8 shows the adapter 300 with a first section 332*a* (e.g., a first arm) and a second section 332*b* (e.g., a second arm), which are separated by a slit 330, and the adapter 300 can have another slit opposite of the slit that is visible in FIG. 8. The adapter 300 can have 2 arms, 3 arms, 4 arms, 5 arms, 6 arms, or any other suitable number of separate arms. In some embodiments, the proximal portion 302 can be a continuous sidewall without breaks (e.g., an annular sidewall).

Figure 9:
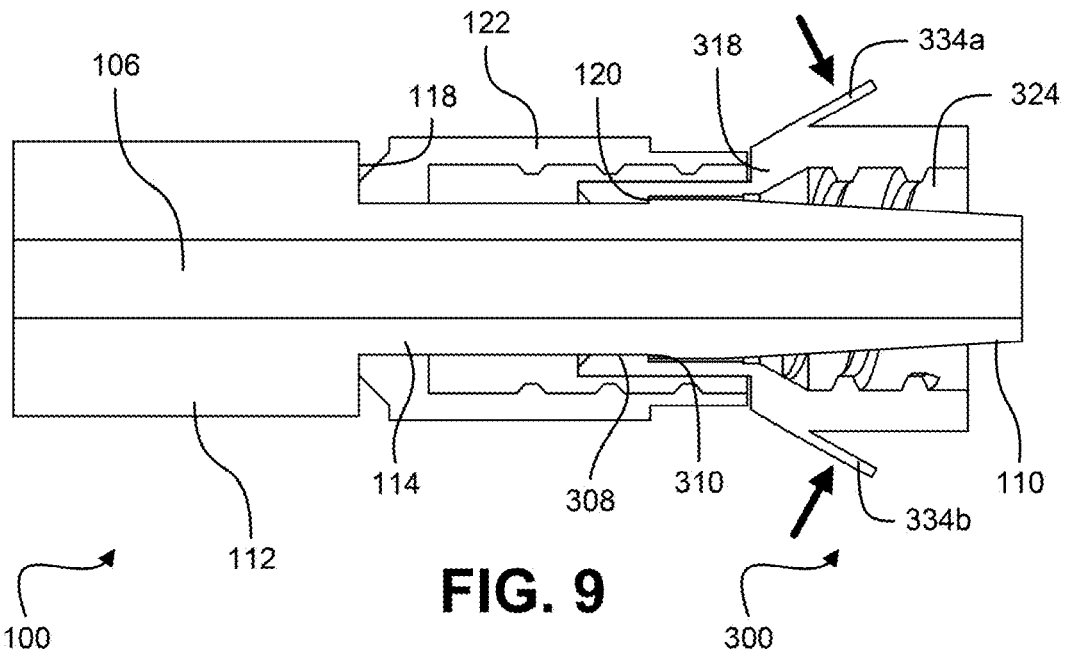
FIG. 9 is a cross-sectional view showing an example embodiment of an adapter coupled to a connector.

In some embodiments, the adapter 300 can be detachable from the connector 100. FIG. 9 is a cross-sectional view showing an example embodiment of an adapter 300 coupled to a connector 100, where the adapter 300 is configured to be removable from the connector 100. The adapter 300 can have one or more arms 334*a*, 334*b*, which can be manipulated (e.g., pressed or pulled) to apply a force that flexes the proximal portion 302 of the adapter 300 laterally outward. This can facilitate the step 310 on the flange 308 or protrusion(s) to disengage from the step 120 on the projection 114, so that the adapter 300 can be moved distally relative to the connector 100 for disconnection. The removable adapter 300 features can use the slit 330 or separate sections 332*a*, 332*b* or arms of FIG. 8, which can facilitate flexing of the proximal portion 302 for disengagement. A continuous proximal portion 302 could also be used, in some embodiments. As shown in FIG. 9, a first arm 334*a* can be disposed on a first side adapter, and a second arm 334*b* can be disposed on a second side of the adapter 300. The arms 334*a*, 334*b* can extend outwardly and distally from the body of the adapter 303 (e.g., from a portion of the adapter 300 where the proximal portion 302 transitions to the distal portion 304, from a proximal part of the distal portion 304, or any other suitable location). To disconnect the adapter 300 from the connector 100, the user can apply a force as shown by the arrows in FIG. 9, which force can be directed laterally inward and/or distally, such as be pinching the arms 334*a*, 334*b* together between the thumb and finger on one hand, in some cases while holding the connector 100 with the other hand, and pulling the adapter 300 and connector 100 apart. The force can be transferred through the adapter to move opposing portions of the flange 308 or opposing protrusion apart, so that the step 310 can disengage from the step 120, for removal of the adapter 300 from the connector 100. Pressing the arm 334*a* laterally inward can cause the arm 332*a* (shown in FIG. 8) to move laterally outward, and/or pressing the arm 334*b* laterally inward can cause the arm 332*b* (shown in FIG. 8) to move laterally outward. In some embodiments, the adapter can include only one arm 334*a*, or any suitable number of arms can be used, such as 2 arms, 3 arms, 4 arms, or more. In some embodiments, the one or more arms 334*a*, 334*b* can be used when attaching the adapter 300 to the connector 100. For example, the user can press the one or more arms 334*a*, 334*b* laterally inward while advancing the projection 114 into the adapter 300, so that the proximal portion 302 of the adapter 300 flexes, or is otherwise displaced, to facilitate the second portion 116*b* of the projection 114 from passing into the proximal portion 302 of the adapter 300. The one or more arms 334*a*, 334*b* can be released to let the flange 308 or protrusion(s) engage with the connector 100, as discussed herein. In some embodiments, the adapter 300 can be configured to not be removable from the connector 100 once coupled thereto.

In some instances where the connector 100 is coupled to connector 200 using the collar 122 (e.g., as shown in FIG. 5), unintended rotation of the collar 122 relative to the body portion 112 (or relative to the projection 114) of the connector 100 can cause the connection between the connectors 100, 200 to leak. For example, the collar 122 and/or the body portion 112 can be accidentally bumped or pressed or otherwise contacted in a manner that can cause the collar 122 to rotate relative to the body portion 112. A friction engagement between the male luer 110 and the female luer 204 can impede the proximal portion 202 from rotating with the collar 122 when the collar 122 is initially rotated relative to the body portion 112 or projection 114. Thus, the collar 122 can rotate relative to the proximal portion 202, which can cause the proximal portion 202 to move distally away from the connector 100 because of the threaded engagement between the threading 128, 206, which can cause the male luer 110 to disengage from the female luer 204, which can result in leakage. In some instances, rotation of the collar 122 relative to the body portion 112 or projection 114 can cause the connector 200 to move distally until the connector fully disengages from the connector 100.

Figure 10:
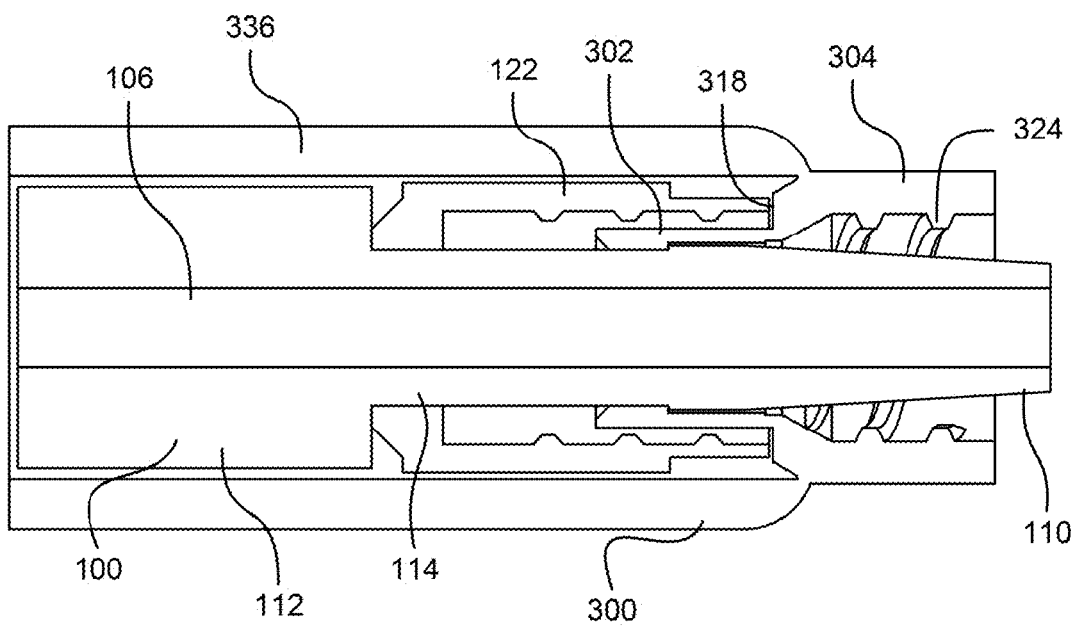
FIG. 10 shows an example embodiment of a connector coupled to an adapter.

In some embodiments, the adapter 300 can be configured to impede unintended rotation relative to the body portion 112 or projection 114. FIG. 10 shows an example embodiment of a connector 100 coupled to an adapter 300 that is configured to impede rotation of the adapter 300 relative to the body portion 112 of the connector 100. The adapter 300 can include a shroud 336, which can be configured to cover or at least partially surround the body portion 112 and/or projection 114 of the connector 100. The shroud 336 can shield the body portion 112 from being bumped or otherwise manipulated in a manner that would cause it to rotate relative to the adapter 300. The shroud 336 can extend proximally past the proximal end of the body portion 112 (e.g., as shown in FIG. 10), or the shroud 336 can extend to be substantially flush with the proximal end of the body portion 112. In some embodiments, the shroud 336 can extend proximally to cover only a portion of (e.g., a majority of) the body portion 112, but without extending all the way to the proximal end of the body portion 112. The shroud 336 can extend from the distal portion 302 of the adapter 300 (e.g., from a proximal part of the distal portion 304, or any other suitable location) or from a portion of the adapter 300 where the proximal portion 302 transitions to the distal portion 304. The shroud 336 can extend from a location on the body of the adapter 300 that is distal of the collar 122 and/or distal of the surface or step 318 that is configured to limit distal movement of the collar 122. The inner diameter of the shroud 336 can be larger than the outer diameter of the body portion 112, larger than the outer diameter of the collar 122. The inner diameter of the shroud 336 can be large enough that a distal portion of the collar 122 can be received into the recess between the proximal portion 302 of the adapter 300 and the shroud 336.

Figure 11:
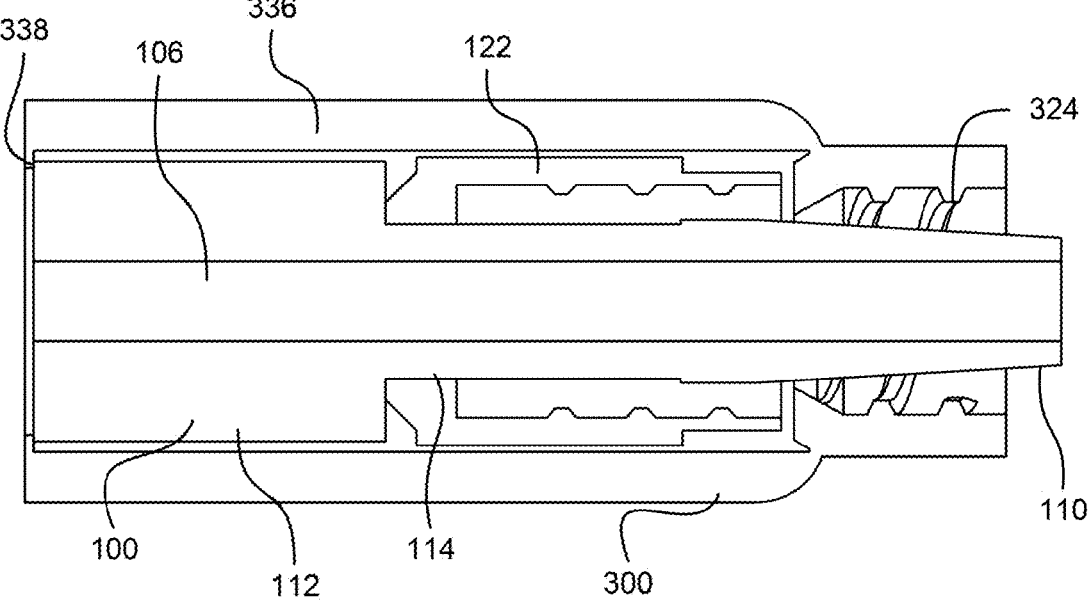
FIG. 11 shows a cross-sectional view of an example embodiment of a connector attached to an adapter that includes a shroud.

FIG. 11 shows a cross-sectional view of an example embodiment of a connector 100 attached to an adapter 300 that includes a shroud 336 similar to FIG. 10. The adapter 300 can include a flange 338 or protrusion(s) that are configured to engage with the body portion 112 of the connector to couple the adapter 300 to the connector 100. The flange 338 or protrusion(s) can extend laterally inward from the inside of the shroud 336 (e.g., at the proximal end of the shroud 336). The shroud 336 can be moved proximally relative to the connector 100 so that the flange 338 or protrusion(s) can pass over the collar 122 and/or the body portion 112 until they reach the proximal end of the body portion 112, at which point the flange 338 or protrusion(s) can snap into engagement with the proximal end of the body portion 112 to attach the adapter 300 to the connector 100. In some embodiments, the adapter 300 does not engage the projection 114 (e.g., the step 120). In some embodiments, the proximal portion 302 that is configured to engage the projection 114 can be omitted, as shown in FIG. 11. The shroud 336 can be the proximal portion of the adapter 300 that is configured to engage the connector 100.

Figure 12:
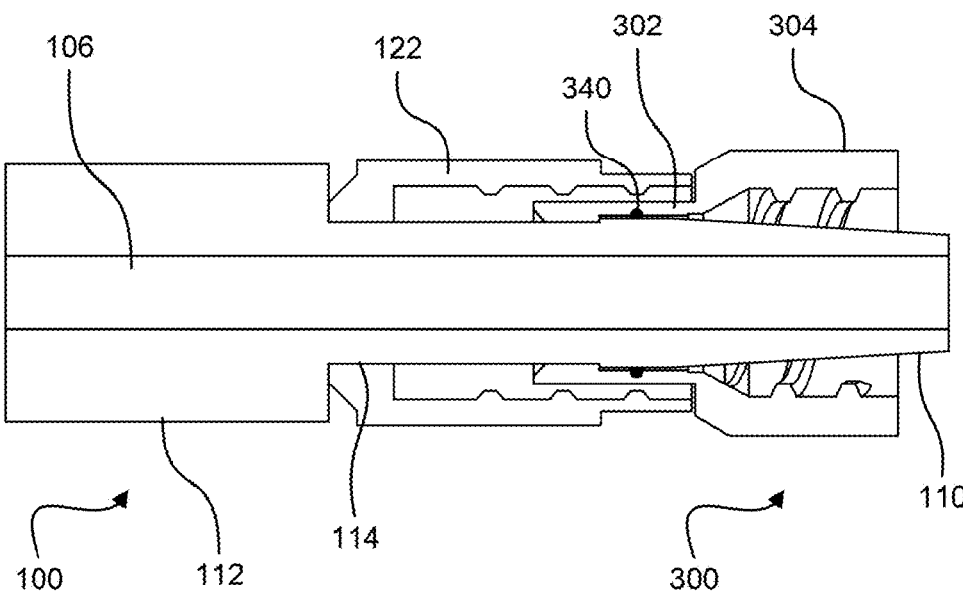
FIG. 12 shows an example embodiment of a connector coupled to an adapter with a seal element.

FIG. 12 shows an example embodiment of a connector 100 coupled to an adapter 300 with a seal element 340 configured to form a substantially fluid-tight seal between the adapter 300 and the connector 100. The seal element 340 can be an O-ring or gasket in some embodiments. The O-ring seal element 340 can be seated in a recess (e.g., an annular recess) on the inner side of the proximal portion 302 of the adapter 300, or on a recess (e.g., an annular recess on the outer side of the projection 114 of the connector 100. The seal element 340 can be compressed between the inner side of the proximal portion 302 of the adapter 300 and the outer side of the projection 114. In some embodiments, multiple seal elements 340 (e.g., O-rings) can be used, which can improve the seal or can function as a backup or failsafe. In some embodiments, the adapter 300 can have slit(s) 330 similar to those discussed in connection with FIG. 8, but the slit(s) can stop before reaching the seal element 340.

Figure 13:
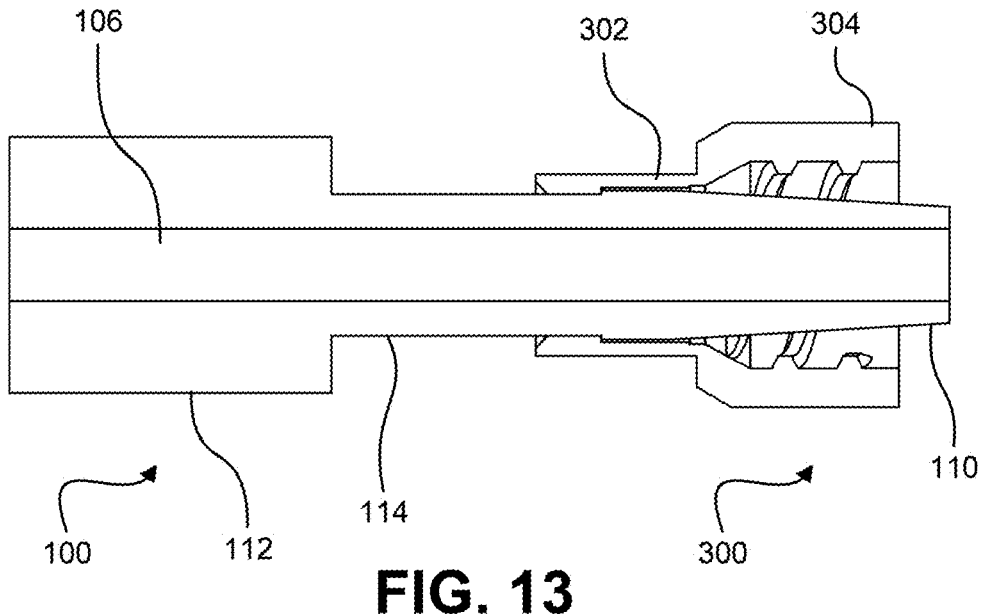
FIG. 13 shows an example embodiment of an adapter coupled a connector.
Figure 14:
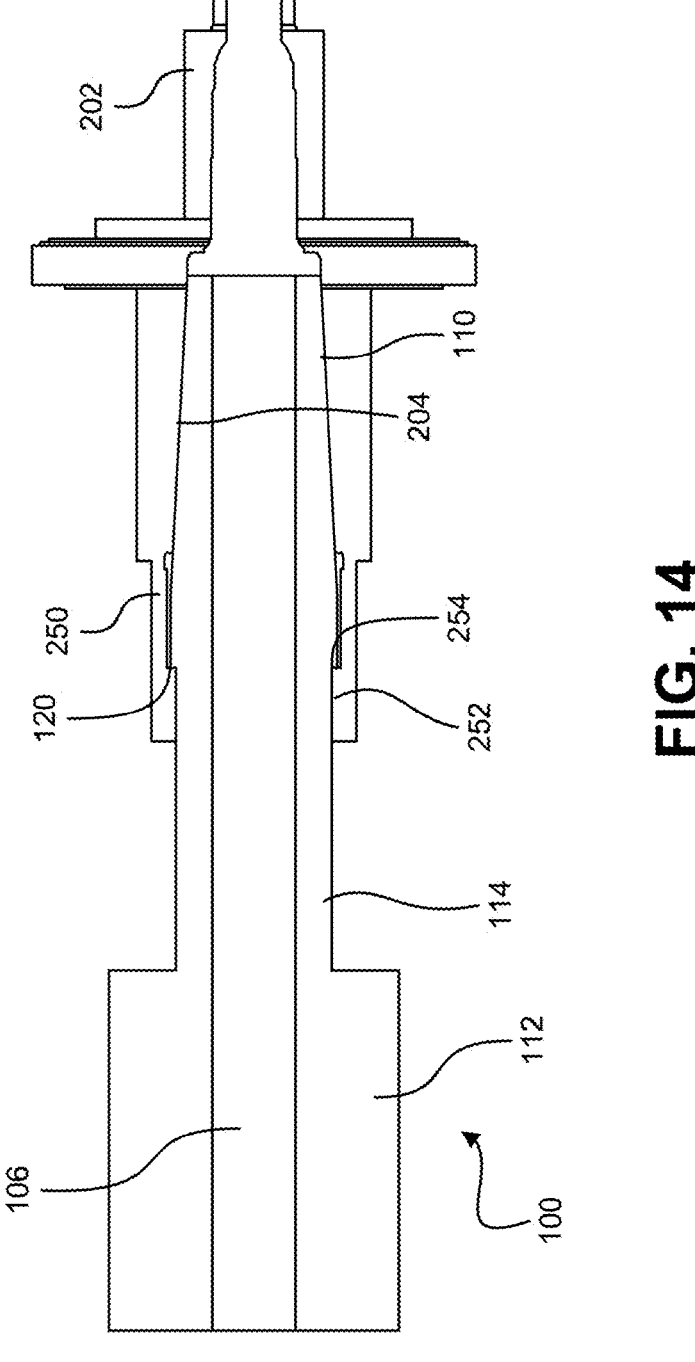
FIG. 14 shows an example embodiment of a connector coupled to a connector.

FIG. 13 shows an example embodiment of an adapter 300 coupled a connector 100 that does not include the collar 122. The embodiment of FIG. 13 can function similar to other embodiments disclosed herein, except that the collar 122 can be omitted. FIG. 14 shows an example embodiment of a connector 100 coupled to a connector 200 that has features similar to the adapter 300 incorporated into the proximal portion 202 of the connector 200. In FIG. 14, the proximal portion 202 is the only portion of the connector 200 that is shown, and the other components of the connector 200 are omitted from view. The other components of the connector 200 can have features similar to the embodiments disclosed in the '712 Publication. In FIG. 14, the collar 122 is omitted from the connector 100, but some embodiments of the connector 100 can include the collar 122, or any of the other features disclosed herein. The proximal portion 202 of the connector 200 can include a female luer 204, which can have a tapered inner surface configured to substantially seal with the outer tapered surface of the male luer 110. The proximal portion 202 can include an engagement portion 250, which can extend proximally of the female luer 204. The engagement portion 250 can have features similar to the proximal portion 302 of the adapter 300 in the embodiments disclosed herein. The engagement portion 250 can have one or more sidewalls, which can at least partially surround an interior chamber. The engagement portion 250 can have the general shape of a hollow cylinder. The engagement portion 250 can have a flange 252 or protrusion(s), such as at the proximal end thereof, which can form a step 254 and can engage a step 120 on the projection 114, such as to couple the connector 100 to the proximal portion 202 of the connector 200. The engagement portion 250 can include any combination of the various other features disclosed in connection the adapter 300, such as release elements, one or more slits, one or more seal elements, or a shroud. The adapters 300 can also include any suitable combination of these features.

Figure 15:
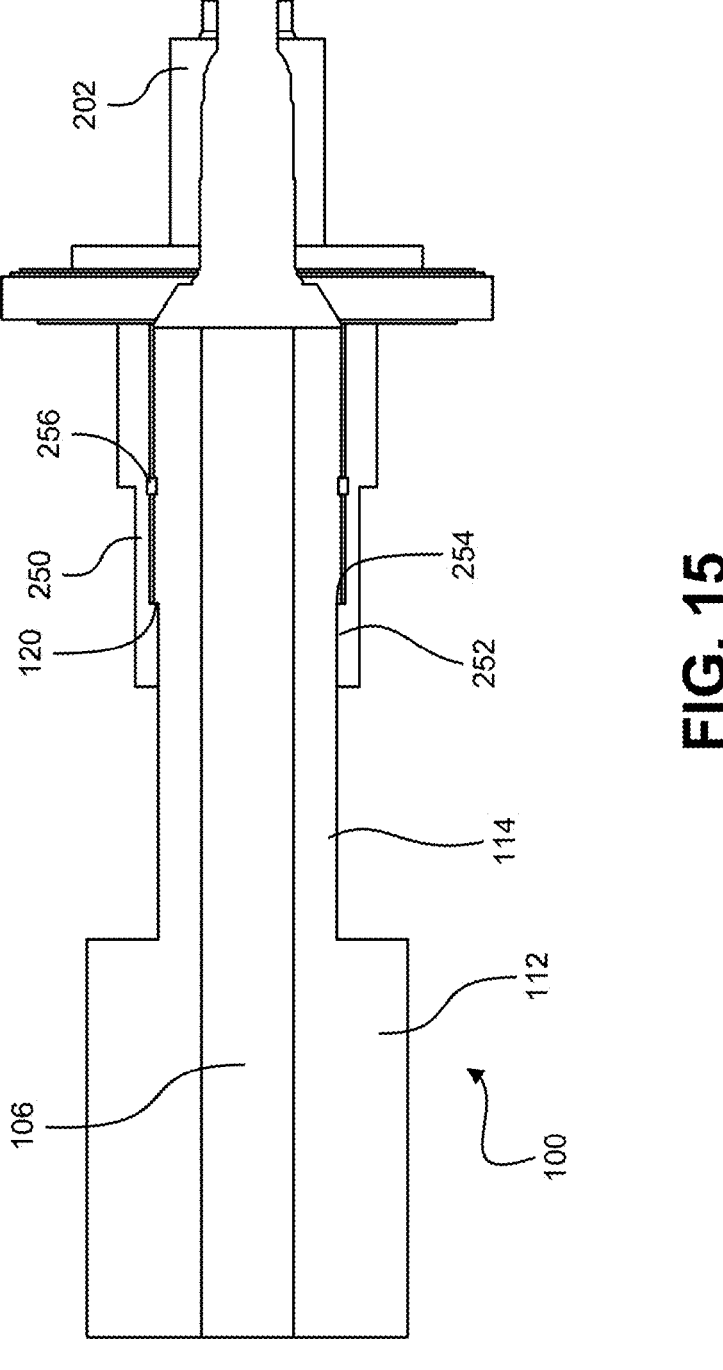
FIG. 15 is a cross-sectional view of an example embodiment of a first connector coupled to a portion of a second connector.

FIG. 15 shows an example embodiment of a connector 100 coupled to a proximal portion 202 of a connector 200. The proximal portion 202 can have an engagement portion 250, which can have features similar to the engagement portion embodiments disclosed in connection with FIG. 14. In some embodiments, the male luer 110 and the female luer 204 can be omitted. The projection 114 of the connector 100 and/or the inside of the proximal portion 202 of the connector 200 can have one or more seal elements 256, which can include an O-ring or gasket. The O-ring seal element 256 can be seated in a recess (e.g., an annular recess) on the inner side of the proximal portion 202 of the connector 200, or on a recess (e.g., an annular recess on the outer side of the projection 114 of the connector 100. The seal element 256 can be compressed between the inner side of the proximal portion 202 of the connector 202 and the outer side of the projection 114. In some embodiments, multiple seal elements 256 (e.g., O-rings) can be used.

Figure 16:
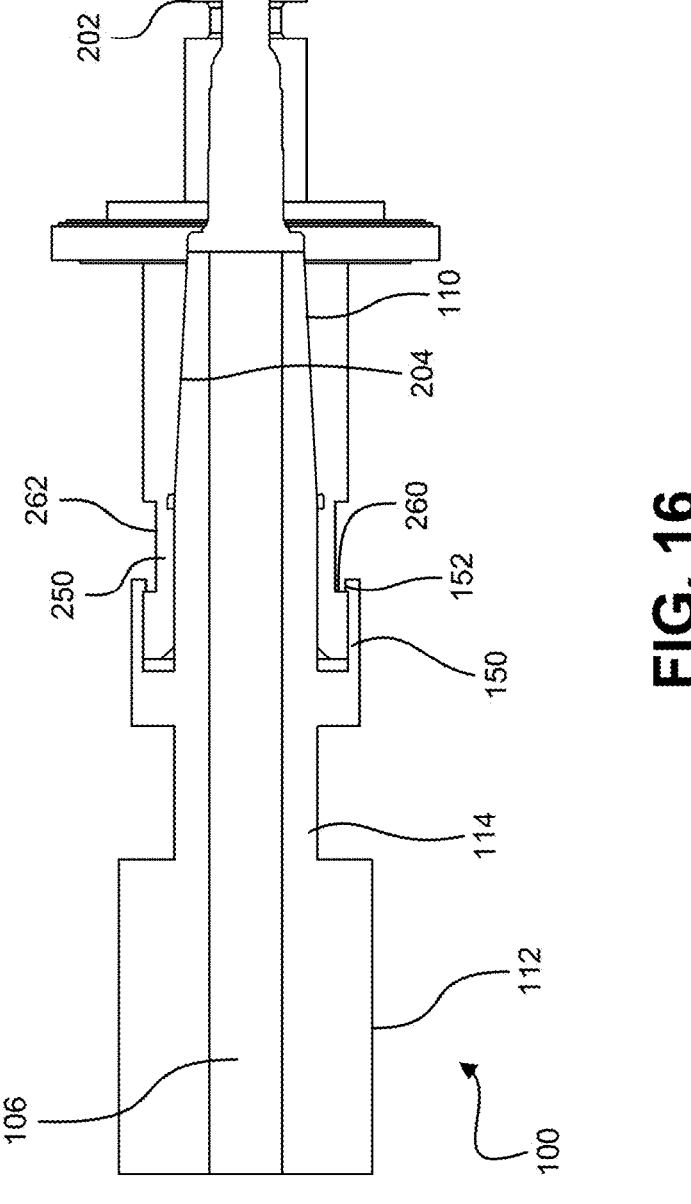
FIG. 16 is a cross-sectional view of an example embodiment of a first connector coupled to a portion of a second connector.

FIG. 16 shows an example embodiment of a connector 100 coupled to a connector 200, where the connector 100 has one or more arms 150 engage with the engagement portion 250 of the proximal portion 202 to couple the connectors 100, 200. The engagement portion 250 of the connector 200 can have a step 260, which can be defined by a recess 262 (e.g. an annular recess). The connector 100 an have one or more arms 150 or an annular shroud, that can extend distally, and can be spaced away from the projection 114, so that the engagement portion 250 of the connector 200 can be received into a recess between the projection 114 and the one or more arms 150 or shroud. The arms can extend from the projection 114, or from the body portion 112, or any other suitable location on the connector 100. The one or more arms 150 or shroud can have a flange 152 or protrusion(s) that extend laterally inward, and can be configured to engage with the step 260 on the connector 200 to couple the connector 100, 200. The connector 100 can include various features disclosed herein such as a release mechanism, one or more seal elements, one or more slits, etc. for the engagement features.

FIGS. 17A-17F show an example embodiment of a process of using the adapter 300 to couple a connector 200 to another connector 100. In some embodiments, the adapter 300 can be first coupled to the connector 100 and then to the connector 200. At FIG. 17A, the user can access the adapter 300. In some cases, the user can open a blister pack or other sealed package containing the adapter 300. The adapter 300 can have a cap 350 attached thereto. The cap 350 can have an engagement feature 352 (e.g., a flange, lug, protrusion, or thread) that is configured to engage the threading 324 of the adapter 300. For example, the cap 350 can be threaded into the distal side 304 of the adapter 300. The cap 350 can have a side wall 354, which can at least partially, or fully, surround an inner cavity. The side wall 354 can be generally cylindrical in shape. The side wall 354 can have ribs or texture to facilitate gripping by the user, such as when disengaging the cap 350, as discussed herein. The cap 350 can have an open bottom side 356. The cap 350 can have a closed top side 358.

Figure 17C:
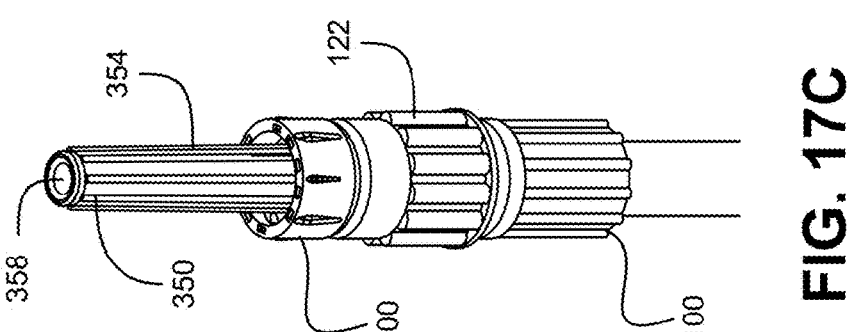
FIGS. 17A-17F show an example embodiment of a process of using the adapter to couple a first connector to a second connector.
Figure 17B:
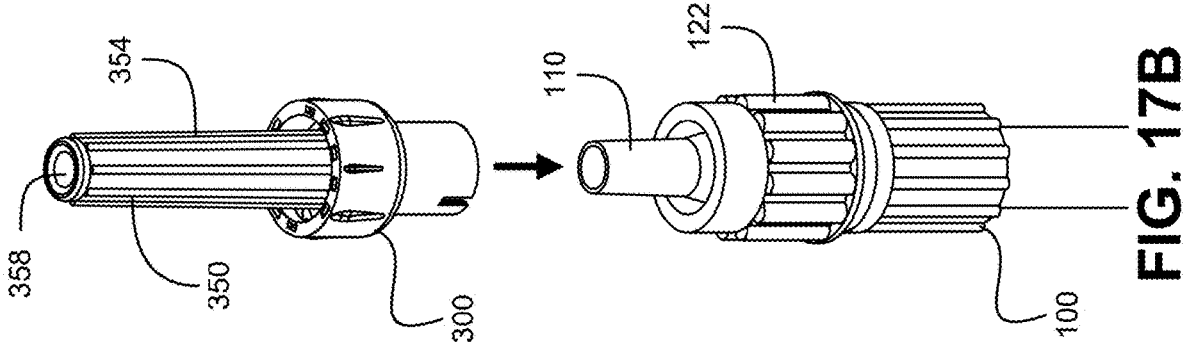
Figure 17A:
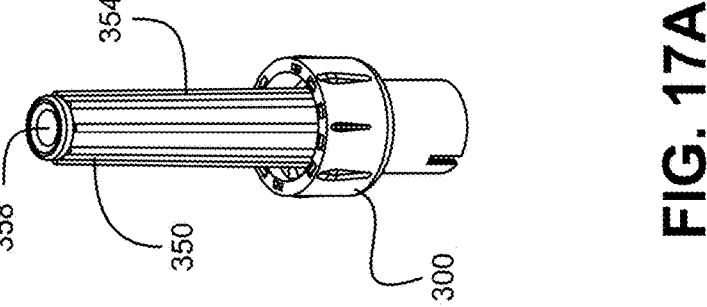

At FIG. 17B, the adapter 300 can be coupled to the connector 100. The adapter 300 can be advanced axially onto the male luer 110 of the connector 100. The male luer 110 of the connector 100 can insert into the proximal end 302 of the adapter 300, and can extend through the interior of the adapter 300. The end of the male luer 110 can extend past the distal end of the adapter 300. In some cases, the male luer 110 can insert into the cap 350 as the adapter 300 is attached to the connector 100. As the adapter 300 is advanced, the male luer 110 can extend through the open end 356 of the cap 350 and can extend into the interior cavity of the cap 350. The adapter 300 can be advanced onto the connector 100 until the adapter 300 attaches onto the connector 100, such as by the flange 308 or protrusion snapping onto the step 120 on the connector 100. The user can push the collar 122 of the connector 100 proximally, such as to make room for the adapter 300 to couple with the connector 100, such as to expose the step 120. In some embodiments, the adapter 300 can push the collar 122 proximally as the adapter 300 is advanced proximally onto the connector 100. The proximal portion 302 of the adapter 300 can extend into the inner cavity of the collar 122 as the adapter 300 is advanced proximally onto the connector 100. The adapter 300 can be pressed onto the male luer 110 with axial motion until it snaps into engagement with the connector 100. In some cases, the adapter 300 can be rotatable during engagement, and/or after being coupled to the connector 100, but rotation of the adapter 300 does not cause engagement or disengagement between the adapter 300 and the connector 100. FIG. 17C shows the adapter 300 coupled to the connector 100.

Figure 17F:
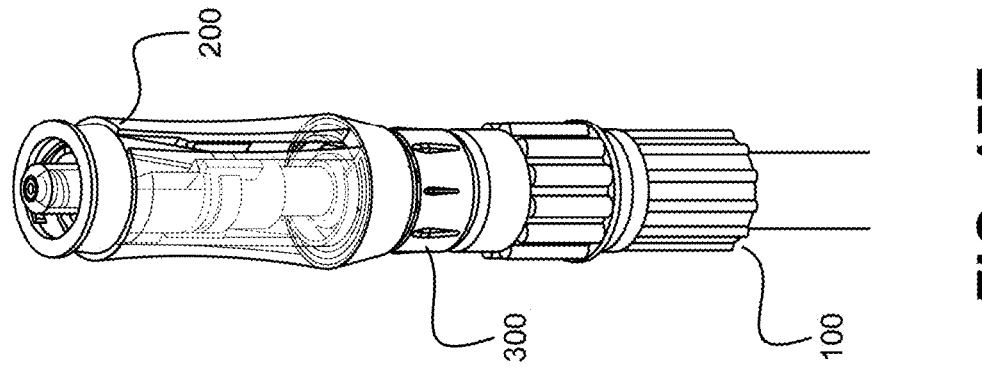
Figure 17E:
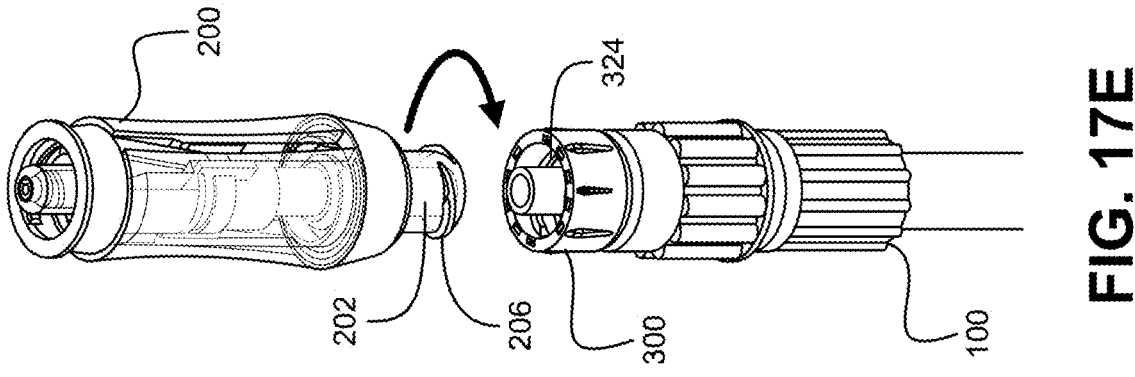
Figure 17D:
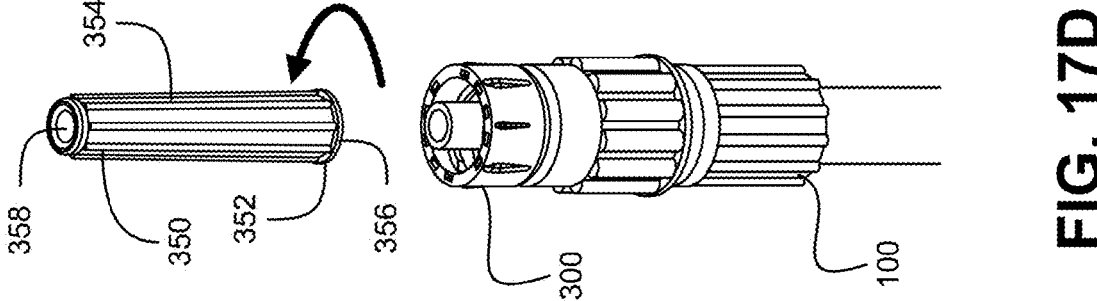

At FIG. 17D, the cap 350 can be removed from the adapter 300. For example, the user can grip the side wall 354 of the cap 350 and can rotate the cap 350 to unthread the cap 350 from the adapter 300. The user can also grip the outside of the distal portion 304 of the adapter 300, which can have ridges or texture to facilitate gripping. Removing the cap 350 from the adapter 300 can also cause the cap 350 to disengage from the connector 100 as well, in some embodiments. For example, the male luer 110 of the connector 100 can withdraw out of the inner cavity of the cap 350 as the cap 350 is removed. In some embodiments, the cap 350 could be removed before the adapter 300 is coupled to the connector 100.

At FIG. 17E, the connector 200 can be coupled to the adapter 300. The user can access the connector 200, such as by opening a blister pack or other sealed package containing the connector 200. The connector 200 can include a proximal portion 202 with threading 206 configured to engage the threading 324 of the adapter 300. The user can rotate the connector 200 relative to the adapter 300, and/or can rotate the adapter 300 relative to the connector 200 so that the threading 206 engages the threading 324 and advances the connector 200 onto the connector 100 and adapter 300. The user can grip the outside of the distal portion of the adapter 300 and/or the outer housing of the connector 200 to provide the rotation. As the connector 200 advances proximally and/or as the connector 100 and adapter 300 advance distally, the male luer 110 of the connector 100 can engage with a female luer bore 204, which can form a substantially fluid tight seal between the connector 100 and the connector 200. The user can rotate connector 200 relative to the adapter 300 until the one or more breakable tabs of the connector 200 break. In this state, the connector 200 can spin freely, such as in both directions, so that the connector 200 is not readily removable from the connector 100 and adapter 300. FIG. 17F shows the connector 200 coupled to the adapter 300 and connector 100, such as in a free-spin or non-removable configuration. The user can connect another connector or other medical implement to the distal end (e.g., male end) of the connector 200. In some embodiments, the connector 200 can already be coupled to the other connector or medical implement at its distal end before it is coupled to the adapter 300 and connector 100.

Figures 18A, 18B, 18C, 18D:
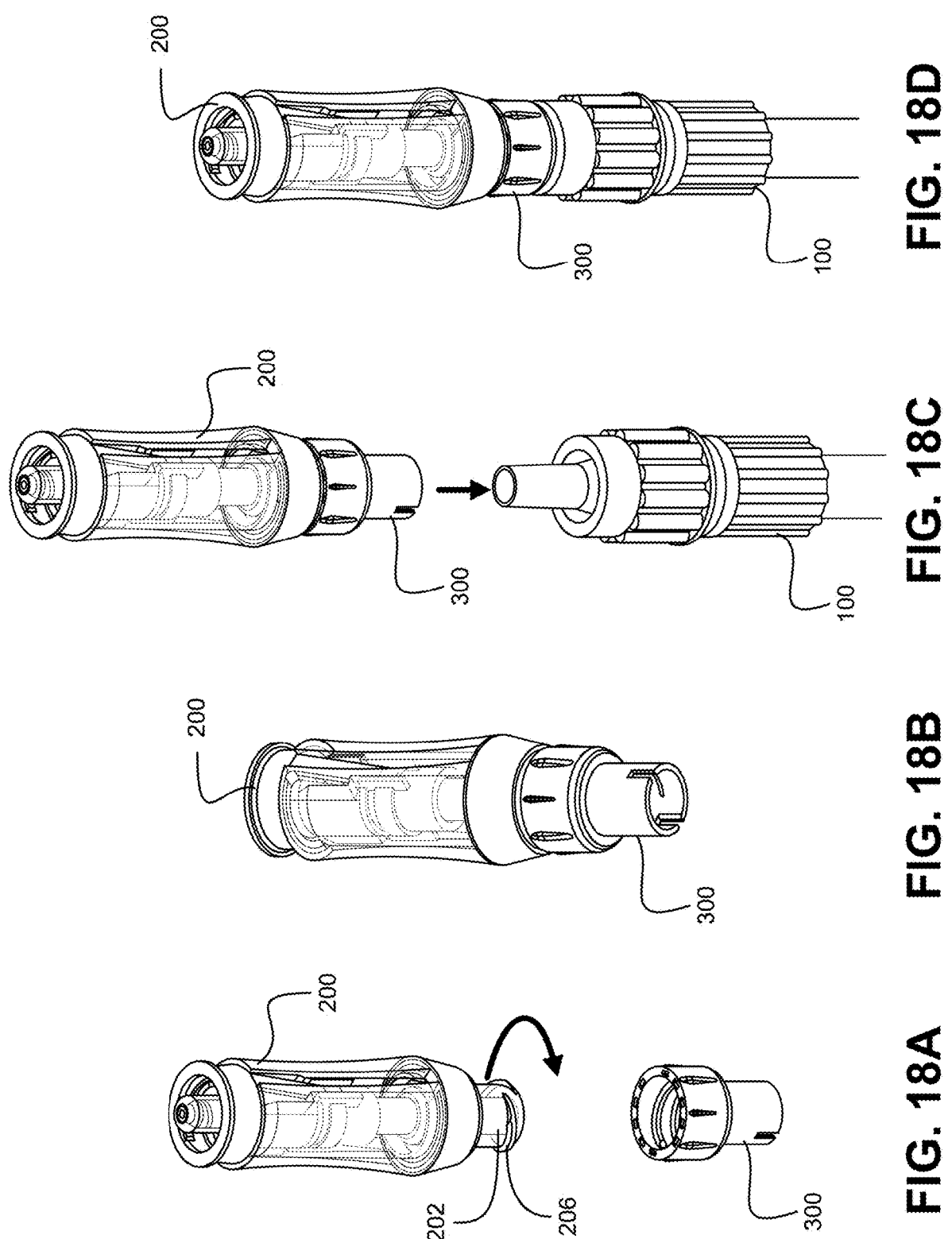
FIGS. 18A to 18D show another example embodiment of a method for using an adapter to couple a first connector to a second connector.

FIGS. 18A to 18D show another example embodiment of a method for using the adapter 300 to couple the connector 200 the connector 100. In some embodiments, the adapter 300 can be first coupled to the connector 200 and then to the connector 100. At FIG. 18A, the user can access the adapter 300 and the connector 200. The user can attach the adapter 300 to the connector 200. For example, the user can insert the end of the proximal portion 202 into the distal end of the adapter 300, and the user can rotate the connector 200 relative to the adapter 300 and/or rotate the adapter 300 relative to the connector 200 so that the threading 206 engages the threading 324. In some embodiments, the user can continue rotating the connector 200 in a first direction (e.g., clockwise) relative to the adapter 300 until the one or more breakable tabs of the connector 200 break, which can put the connector 200 into a free-spin configuration. In the free-spin configuration, rotation of connector 200 housing in a second direction (e.g., counter-clockwise) relative to the adapter 300 does not disengage the connector 200 from the adapter 300. FIG. 18B shows the connector 200 coupled to the adapter 300. The adapter 300 of FIG. 18 could come with a cap 350, which can be removed before the adapter 300 is coupled to the connector 200. In some embodiments, the connector 200 and/or the adapter 300 can have a stop that is configured to prevent the adapter 300 from rotating too far up the proximal portion 202 of the connector 200. The stop can position the adapter 300 on the proximal portion 202 of the connector 200 so that the female luer 204 of the connector 200 will sealingly engage with the male luer 110 of the connector 110 when the adapter 300 engages with (e.g., snaps onto) the connector 100. The stop can be an end of the threading 324 and/or 206, or the stop can be the distal end of the adapter 300 abutting against a surface of the connector 200, or the like.

At FIG. 18C, the adapter 300 can connector 200 can be coupled to the connector 100. The male luer 110 of the connector 100 can be inserted through the proximal end of the adapter 300. The adapter 300 and connector 200 can be advanced axially until the adapter engages with the connector 100, such as by a snap-fit engagement. For example, the flange 308 or protrusion can engage with the step 120 to hold the adapter 300 onto the connector 100, as discussed herein. The adapter 300 can push the collar 122 proximally when it engages the connector 100, such as to permit the adapter 300 to engage with the step 120. The proximal portion of the adapter 300 can be inserted into the distal end of the collar 122 when the adapter 300 is coupled to the connector 100. FIG. 18D shows the connector 200 and adapter 300 coupled to the connector 100.

In some embodiments, the adapter 300 can be pre-attached to the connector 200. Accordingly, FIG. 18A can be omitted. In some cases, the user can access the connector 200 with the adapter 300 already attached thereto. In some embodiments, the adapter can be omitted 300 can the snap engagement features can be incorporated into the proximal portion 202 of the connector 200, such as similar to FIGS. 14-16. In some embodiments, the connector 200 does not have one or more breakable tabs, and the proximal portion 202 can always be in a free-spin configuration relative to the housing of the connector 200.

When the adapter 300 couples the connector 200 to the connector 100, the adapter 300 can spin freely in both directions relative to the connector 100. The housing of the connector 200 can spin freely in both directions relative to the adapter 300. In some cases, the proximal portion 202 of the connector 200 can rotate with the adapter 300. The proximal portion 202 of the connector can spin freely in both directions relative to the housing of the connector 200, such as after the one or more breakable tabs have been broken. The housing of the connector 200 can spin freely in both directions relative to the connector 100.

Various alternatives and combinations of the disclosed features can be used. Also, the proportions and ratios of the sizes of various components, edges, and surfaces that are shown in the Figures are intended to form part of this disclosure, even when not specifically discussed.

Unless the context clearly requires otherwise, throughout the description and the claims, the words "comprise," "comprising," "include," "including," and the like are to be construed in an inclusive sense, as opposed to an exclusive or exhaustive sense; that is to say, in the sense of "including, but not limited to." The words "coupled" or connected," as generally used herein, refer to two or more elements that can be either directly connected, or connected by way of one or more intermediate elements. Additionally, the words "herein," "above," "below," and words of similar import, when used in this application, shall refer to this application as a whole and not to any particular portions of this application. Where the context permits, words in the Detailed Description using the singular or plural number can also include the plural or singular number, respectively. The words "or" in reference to a list of two or more items, is intended to cover all of the following interpretations of the word: any of the items in the list, all of the items in the list, and any combination of the items in the list. All numerical values provided herein are intended to include similar values within a range of measurement error.

Although this disclosure contains certain embodiments and examples, it will be understood by those skilled in the art that the scope extends beyond the specifically disclosed embodiments to other alternative embodiments and/or uses and obvious modifications and equivalents thereof. In addition, while several variations of the embodiments have been shown and described in detail, other modifications will be readily apparent to those of skill in the art based upon this disclosure. It is also contemplated that various combinations or sub-combinations of the specific features and aspects of the embodiments may be made and still fall within the scope of this disclosure. It should be understood that various features and aspects of the disclosed embodiments can be combined with, or substituted for, one another in order to form varying modes of the embodiments. Any methods disclosed herein need not be performed in the order recited. Thus, it is intended that the scope should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Any headings used herein are for the convenience of the reader only and are not meant to limit the scope.

Further, while the devices, systems, and methods described herein may be susceptible to various modifications and alternative forms, specific examples thereof have been shown in the drawings and are herein described in detail. It should be understood, however, that the disclosure is not to be limited to the particular forms or methods disclosed, but, to the contrary, this disclosure covers all modifications, equivalents, and alternatives falling within the spirit and scope of the various implementations described. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including ambient temperature and pressure.

The following is claimed:

1. A method comprising:

accessing a first medical connector that comprises:

a proximal end with a proximal opening;

a distal end with a distal opening, a fluid pathway between the proximal end and the distal end;

a body portion;

a projection extending distally from the body portion, wherein the projection comprises a step, and wherein the projection comprises a male luer with a tapered outer surface configured to engage a tapered inner surface of a female luer; and a collar substantially surrounding the projection, the collar having internal threading;

accessing an adapter that comprises:

a proximal portion having one or more protrusions that extend inward; and a distal portion having internal threading;

coupling the adapter to the first medical connector by:

inserting the projection into the proximal portion of the adapter; and advancing the adapter axially in a proximal direction until the one or more protrusions engage the step on the projection; and accessing a second medical connector that comprises:

a distal end with a distal opening, a proximal end with a proximal opening, wherein the proximal end includes a female luer and external threading; and a fluid pathway between the proximal end and the distal end; and coupling the second medical connector to the adapter by:

inserting the proximal end of the second medical connector into the distal portion of the adapter; and rotating the second medical connector relative to the adapter so that the external threading on the proximal end of the second medical connector engages the internal threading on the distal portion of the adapter so that the male luer of first medical connector sealingly engages the female luer of the second medical connector.

2. The method of claim 1, wherein the proximal portion of the adapter is inserted into the collar as the adapter is advanced axially.

3. The method of claim 1, further comprising rotating the second medical connector relative to the adapter further so that one or more breakable elements on the second medical connector break to transition the second medical connector to a free-spin configuration.

4. The method of claim 1, wherein the adapter does not engage the internal threading of the collar.

5. The method of claim 1, wherein the internal threading of the collar is configured to engage the external threading of the second medical connector.

6. The method of claim 5, wherein the male luer of first medical connector sealingly engages the female luer of the second medical connector without the internal threading of the collar engaging the external threading of the second medical connector.

7. The method of claim 1, wherein the proximal portion of the adapter has an outer diameter that is smaller than an inner diameter of the collar so that the proximal portion of the adapter fits into a recess between the collar and the projection and wherein the distal portion of the adapter has an outer diameter that is larger than the inner diameter of the collar.

8. The method of claim 7, wherein the distal portion of the adapter extends distally past the collar when the proximal portion of the adapter fits into a recess between the collar and the projection.

9. The method of claim 1, wherein the distal portion of the adapter extends distally past the collar when the male luer of first medical connector is sealingly engaged with the female luer of the second medical connector.

10. The method of claim 1, wherein the one or more protrusions comprise an annular flange.

11. The method of claim 1, wherein coupling the adapter to the first medical connector engages a seal between the adapter and the projection.

12. A method comprising:

accessing a first medical connector that comprises:

a distal end with a distal opening, a proximal end with a proximal opening, wherein the proximal end includes a female luer and external threading;

a fluid pathway between the proximal end and the distal end; and an adapter comprising:

a distal portion having internal threading that engages the external threading of the proximal end; and a proximal portion having one or more protrusions;

accessing a second medical connector that comprises:

a proximal end with a proximal opening;

a distal end with a distal opening, a fluid pathway between the proximal end and the distal end;

a body portion;

a projection extending distally from the body portion, wherein the projection comprises a step, and wherein the projection comprises a male luer with a tapered outer surface; and a collar substantially surrounding the projection, the collar having internal threading;

coupling the second medical connector to the adapter by:

inserting the projection into the proximal portion of the adapter; and advancing the adapter axially in a proximal direction with respect to the second connector until the one or more protrusions engage the step on the projection, and so that the male luer of second medical connector sealingly engages the female luer of the first medical connector.

13. The method of claim 12, wherein the adapter does not engage the internal threading of the collar.

14. The method of claim 12, wherein the internal threading of the collar is configured to engage the external threading of the first medical connector.

15. The method of claim 14, wherein the male luer of second medical connector sealingly engages the female luer of the first medical connector without the internal threading of the collar engaging the external threading of the first medical connector.

16. The method of claim 12, wherein the proximal portion of the adapter has an outer diameter that is smaller than an inner diameter of the collar so that the proximal portion of the adapter fits into a recess between the collar and the projection and wherein the distal portion of the adapter has an outer diameter that is larger than the inner diameter of the collar.

17. The method of claim 12, wherein the distal portion of the adapter extends distally past the collar when the male luer of second medical connector is sealingly engaged with the female luer of the first medical connector.

18. The method of claim 12, wherein the one or more protrusions comprise an annular flange.

19. The method of claim 12, further comprising rotating the first medical connector relative to the adapter so that one or more breakable elements on the first medical connector break to transition the first medical connector to a free-spin configuration.

20. The method of claim 12, wherein coupling the second medical connector to the adapter engages a seal between the adapter and the projection.

* * * * *